US009828418B2

(12) United States Patent
El Menyawi et al.

(10) Patent No.: US 9,828,418 B2
(45) Date of Patent: Nov. 28, 2017

(54) PROCESS FOR ENRICHING IGA

(71) Applicant: CSL BEHRING AG, Bern (CH)

(72) Inventors: Ibrahim El Menyawi, Bern (CH); Marius Loetscher, Gerzensee (CH); Doreen Siegemund, Visp (CH)

(73) Assignee: CSL BEHRING AG, Bern (CH)

( * ) Notice: Subject to any disclaimer, the term of this patent is extended or adjusted under 35 U.S.C. 154(b) by 237 days.

(21) Appl. No.: 14/377,535

(22) PCT Filed: Mar. 8, 2013

(86) PCT No.: PCT/EP2013/054698
§ 371 (c)(1),
(2) Date: Aug. 8, 2014

(87) PCT Pub. No.: WO2013/132053
PCT Pub. Date: Sep. 12, 2013

(65) Prior Publication Data
US 2015/0005476 A1 Jan. 1, 2015

(30) Foreign Application Priority Data
Mar. 9, 2012 (EP) ..................... 12158927

(51) Int. Cl.
*B01D 15/36* (2006.01)
*C07K 16/06* (2006.01)
*C07K 16/00* (2006.01)
*C07K 16/18* (2006.01)

(52) U.S. Cl.
CPC .......... *C07K 16/065* (2013.01); *B01D 15/363* (2013.01); *C07K 16/00* (2013.01); *C07K 16/18* (2013.01)

(58) Field of Classification Search
None
See application file for complete search history.

(56) References Cited

U.S. PATENT DOCUMENTS

| 5,258,177 | A | 11/1993 | Uemura et al. |
| 5,410,025 | A | 4/1995 | Moller et al. |
| 5,500,345 | A * | 3/1996 | Soe ........................ C07K 16/40 435/332 |
| 6,069,236 | A | 5/2000 | Burnouf-Radosevich et al. |
| 6,300,104 | B1 | 10/2001 | Morrison et al. |
| 6,307,028 | B1 | 10/2001 | Lebing et al. |
| 6,646,108 | B1 | 11/2003 | Leibl et al. |
| 6,967,106 | B2 | 11/2005 | Simon |
| 7,597,891 | B2 | 10/2009 | Simon |
| 7,749,721 | B2 | 7/2010 | Alonso-Garcia et al. |
| 7,794,721 | B2 | 9/2010 | Simon |
| 8,021,645 | B2 | 9/2011 | Simon |
| 8,119,104 | B2 | 2/2012 | Simon et al. |
| 8,313,730 | B2 | 11/2012 | Simon et al. |
| 8,709,413 | B2 | 4/2014 | Simon |
| 9,522,184 | B2 | 12/2016 | Von Gunten et al. |
| 9,546,209 | B2 | 1/2017 | Aebi et al. |
| 2003/0082643 | A1 | 5/2003 | Hudson et al. |
| 2004/0132979 | A1 | 7/2004 | Chtourou et al. |
| 2008/0145371 | A1 | 6/2008 | Simon |
| 2008/0145420 | A1 | 6/2008 | Simon |
| 2010/0322872 | A1 | 12/2010 | Perraudin |
| 2013/0210164 | A1* | 8/2013 | Gagnon ................. G01N 1/34 436/177 |
| 2013/0338344 | A1* | 12/2013 | Ramasubramanyan ..... C07K 1/ 165530/389.2 |
| 2014/0348935 | A1 | 11/2014 | Simon |
| 2015/0017181 | A1 | 1/2015 | Kelly et al. |
| 2015/0056180 | A1 | 2/2015 | Corthésy et al. |

FOREIGN PATENT DOCUMENTS

| CN | 1500097 A | 5/2004 |
| EP | 0 413 188 A2 | 2/1991 |
| EP | 0 703 922 A1 | 4/1996 |
| EP | 0 839 915 A1 | 5/1998 |
| JP | 2000-103800 A | 4/2000 |
| WO | WO 94/29334 A1 | 12/1994 |
| WO | WO 95/04081 A1 | 2/1995 |
| WO | WO 97/25352 A1 | 7/1997 |
| WO | WO 98/57993 A1 | 12/1998 |
| WO | WO 99/64462 A1 | 12/1999 |
| WO | WO 00/41721 A1 | 7/2000 |
| WO | WO 02/076502 A1 | 10/2002 |
| WO | WO 02/092632 A1 | 11/2002 |
| WO | WO 03/015817 A2 | 2/2003 |
| WO | WO 2004/012763 A1 | 2/2004 |

(Continued)

OTHER PUBLICATIONS

Malmquist et al. "Characterization of the influence of displacing salts on retention in gradient elution ion-exchange chromatography of proteins and peptides" J. Chromatogr. 1992, 627(1-2), 107-24.*
Leung et al. "Charge-dependent bionding of polymeric IgA1 to human mesangial cells in IgA nephropathy" Kidney International, 59, 2001, 277-285.*
Teschner et al. A new liquid, intravenous immunoglobulin product (IGIV 10%) highly purified by a state-of-the-art process, Vox Sang, 92(1), 2007, 42-55.*
GE Healthcare Life Sciences "Mono Q 5/50 GL" product data sheet, product cod 17/5166-01, 2016, p. 1.*
International Preliminary Report on Patentability and Written Opinion dated Sep. 18, 2014, in PCT International Application No. PCT/EP2013/054698.
English abstract of Nitschmann et al., "107. Vereinfachtes Verfahren zur Gewinnug von humanem Albumin and γ-Globulin aus Blutplasma mittels Alkoholfallung," Helvetical Chimica Acta. (1954), vol. 37, pp. 866-873.
Steinbuch, M. and R. Audran, "The isolation of IgG from Mammalian Sera with the Aid of Caprylic Acid," Archives of Biochemistry and Biophysics (1969), vol. 134, pp. 279-284.

(Continued)

Primary Examiner — Daniel E Kolker
Assistant Examiner — James Rogers
(74) Attorney, Agent, or Firm — Birch, Stewart, Kolasch & Birch, LLP

(57) ABSTRACT

The invention relates to a process for enriching IgA (and IgM) from IgA-comprising material. In particular, it relates to a sequential elution process of an anion exchanger that leads to an advantageous enrichment and separation of monomeric and dimeric IgA.

26 Claims, 12 Drawing Sheets

(56) References Cited

FOREIGN PATENT DOCUMENTS

Figure 1:
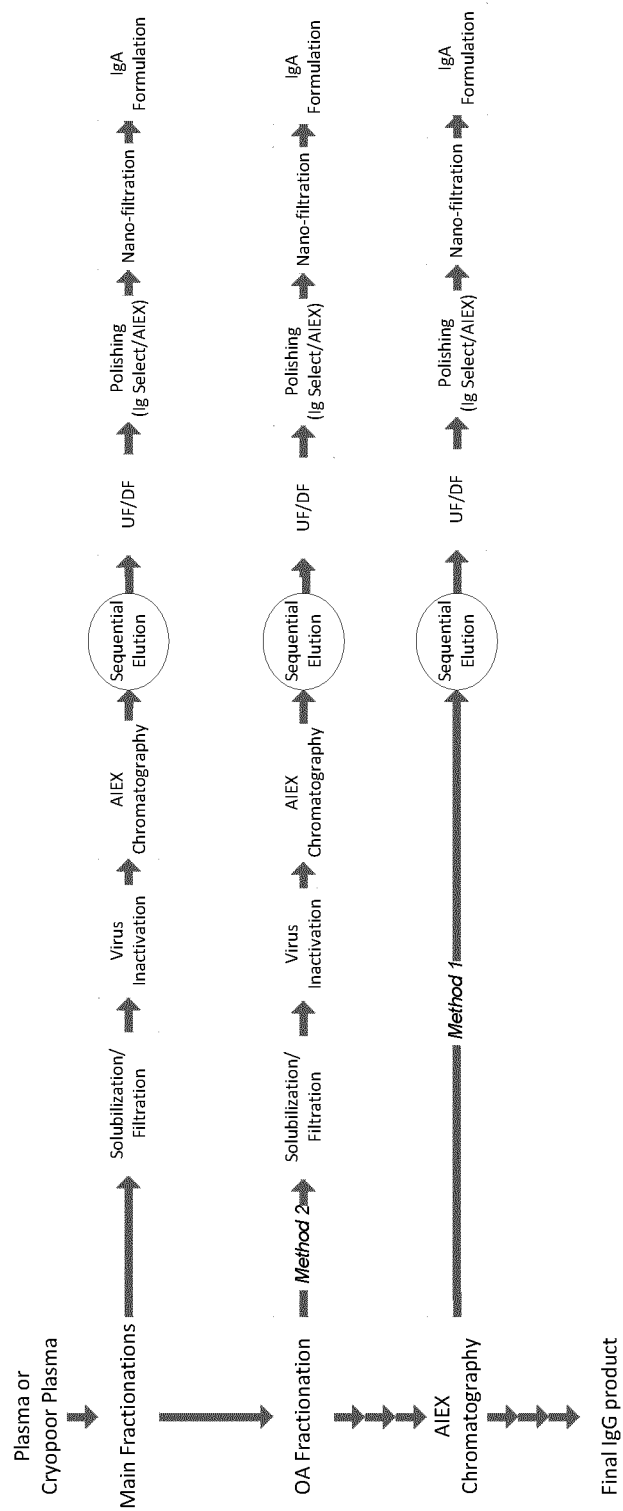

| WO | WO 2005/047337 A1 | 5/2005 |
|---|---|---|
| WO | WO 2009/046168 A1 | 4/2009 |
| WO | WO 2009/139624 A1 | 11/2009 |
| WO | WO 2011/131786 A2 | 10/2011 |

OTHER PUBLICATIONS

Cohn et al., "Preparation and Properties of Serum and Plasma Proteins. IV. A System for the Separation into Fractions of the Protein and Lipoprotein Components of Biological Tissues and Fluids," J. Am. Chem. Soc. (Mar. 1946), vol. 68, pp. 459-475.
Cripps et al., "Isolation of Human IgA and IgM from Normal Serum Using Polyethylene Glycol Precipitation and Affinity Chromatography," Journal of Immunological Methods (1983), vol. 57, pp. 197-204.
Doellgast, G. J. and A. G. Plaut, "Purification of Human IgA by Salt-Mediated Hydrophobic Chromatography," Immunochemistry (1976), vol. 13, pp. 135-139.
Donadoni et al., "Setting of Methods for Analysis of Mucosal Antibodies in Seminal and Vaginal Fluids of HIV Seropositive Subjects from Cambodian and Italian Cohorts," PLoS ONE (Mar. 2010), vol. 5, No. 3, e9920, pp. 1-16.
Eibl et al, "Prevention of Necrotizing Enterocolitis in Low-Birth-Weight Infants by IgA-IgG Feeding," The New England Journal of Medicine (Jul. 7, 1988), vol. 319, No. 1, pp. 1-7.
Extended European Search Report dated Jul. 18, 2012, in European Patent Application No. 12158927.9.
Hammarstrom et al., "Systemic and Topical Immunoglobulin Treatment in Immunocompromised Patients," Immunological Reviews (1994), No. 139, pp. 43-70.
International Search Report and Written Opinion dated Apr. 10, 2013, in PCT International Application No. PCT/EP2013/054698.
Kobyashi et al,. "Separation of Human sIgA1 and sIgA2 by Affinity Chromatography on the Jackfruit Lectin, Jacalin," Adv. Exp. Med. Biol. (1987), vol. 216B, pp. 1193-1197.
Leung et al., "Charge-dependent binding of polymeric $IgA_1$ to human mesangial cells in IgA nephropathy," Kidney International (2001), vol. 59, pp. 277-285.
Liebl et al., "Isolation of Human Serum IgA Using Thiophilic Adsorption Chromatography," Protein Expression and Purification (1995), vol. 6, pp. 408-410.
Luellau et al., "Development of a downstream process for the isolation and separation of monoclonal immunoglobulin A monomers, dimers and polymers from cell culture supernatant," Journal of Chromatography A (1998), vol. 796, pp. 165-175.
Lullau et al., "Development of a bioprocess for murine dimeric IgA production," Biotechnology Techniques (Jun. 1998), vol. 12, No. 6, pp. 425-430.
Oncley et al., "The separation of the Antibodies, Isoagglutinins, Prothrombin, Plasminogen, and β1-Lipoprotein into Subfractions of Human Plasma," J. Am. Chem. Soc. (Feb. 1949), vol. 71, pp. 541-550.
Patent Examination Report No. 1 dated Nov. 22, 2013, in Australian Patent Application No. 2013201388.
Pejaudier et al., "Preparation of Human IgA as By-Product of Routine Fractionation," Vox Sang. (1972), vol. 23, pp. 165-175.
Roque-Barreira, M. C. and A. Campos-Neto, "Jacalin: An IgA-Binding Lectin," The Journal of Immunology (Mar. 1985), vol. 134, No. 3, pp. 1740-1743.
Wiersma et al., "Structural and Functional Analysis of J Chain-Deficient IgM," J. Immunol. (1998), vol. 160, pp. 5979-5989.
Atassi et al., "Molecular Immunology," Aug. 31, 1988, pp. 207-210 (Total 6 pages).
Chinese Office Action and Chinese Search Report, dated Oct. 24, 2016, for Chinese Application No. 201380013075.7, with an English translation.
Japanese Office Action, dated Nov. 15, 2016, for Japanese Application No. 2014-560388, along with an English translation.
Qingyi et al., "Biochemical Experiments of Food Products," South China University of Technology Press, Feb. 1, 2012, pp. 24-26 & 30 (Total 6 pages).
Walsh, "Proteins Biochemistry and Biotechnology," John Wiley & Sons, Mar. 2006, pp. 82 (Total 3 pages).
Aebi et al., "A Protective Epitope of Moraxella catarrhalis Is Encoded by Two Different Genes," Infection and Immunity, vol. 65, No. 11, Nov. 1997, pp. 4367-4377 (Total 12 pages).
Aebi et al., "Phenotypic Effect of Isogenic uspA1 and uspA2 Mutations on Moraxella catarrhalis 035E," Infection and Immunity, vol. 66, No. 7, Jul. 1998, pp. 3113-3119 (Total 8 pages).
Australian Office Communication dated Nov. 25, 2013, for Australian Application No. 2013201393.
Australian Patent Examination Report for Australian Application No. 2013201394, issued Dec. 4, 2013.
Australian Patent Examination Report No. 1, dated Oct. 25, 2013, for Australian Application No. 2013201389.
Bartlett et al., "Antibiotic-Associated Pseudomembranous Colitis Due to Toxin-Producing Clostridia", The New England Journal of Medicine, vol. 298, No. 10, Mar. 9, 1978, pp. 531-534.
Bauer et al., "Alternative strategies for Clostridium difficile infection", International Journal of Antimicrobial Agents, vol. 33, No. S1, 2009, pp. S51-S56.
Berdoz et al., "In vitro comparison of the antigen-binding and stability properties of the various molecular forms of IgA antibodies assembled and produced in CHO cells," Proceedings of the National Academy of Sciences, vol. 96, No. 6, Mar. 16, 1999, pp. 3029-3034.
Blijlevens et al., "Palifermin (recombinant keratinocyte growth factor-1): a pleiotropic growth factor with multiple biological activities in preventing chemotherapy- and radiotherapy-induced mucositis," Annals of Oncology, vol. 18, No. 5, May 2007 (Published online Oct. 9, 2006), pp. 817-826.
Bonner et al., "Solution Structure of Human Secretory Component and Implications for Biological Function," The Journal of Biological Chemistry, vol. 282, No. 23, Jun. 8, 2007, pp. 16969-16980.
Bonner et al., "Solution structure of recombinant human secretory component and its two- and three-domain fragments by scattering, ultracentrifugation and constrained modeling," Molecular Immunology, vol. 44, Jan. 1, 2007, p. 156, abstract only.
Bootsma et al., "Analysis of Moraxella catarrhalis by DNA Typing: Evidence for a Distinct Subpopulation Associated with Virulence Traits," The Journal of Infectious Diseases, vol. 181, 2000 (Electronically published Apr. 13, 2000), pp. 1376-1387.
Brach et al., "Ionizing Radiation Induces Expression of Interleukin 6 by Human Fibroblasts Involving Activation of Nuclear Factor-κB," The Journal of Biological Chemistry, vol. 268, No. 12, Apr. 25, 1993, pp. 8466-8472.
Brandtzaeg, "Mucosal immunity: integration between mother and the breast-fed infant," Vaccine, vol. 21, 2003, pp. 3382-3388.
Brooks et al., "Moraxella catarrhalis Binding to Host Cellular Receptors Is Mediated by Sequence-Specific Determinants Not Conserved among All UspA1 Protein Variants," Infection and Immunity, vol. 76, No. 11, Nov. 2008 (Aug. 4, 2008), pp. 5322-5329 (Total 9 pages).
Chen et al., "A Mouse Model of Clostridium difficile-Associated Disease", Gastroenterology, vol. 135, No. 6, Dec. 2008, pp. 1984-1992.
Chinese Office Action and Search Report with English translations thereof, dated May 6, 2014, for Chinese Application No. 201180060034.4.
Coia, "What is the role of antimicrobial resistance in the new epidemic of Clostridium difficile?", International Journal of Antimicrobial Agents, vol. 33, No. S1, 2009, pp. S9-S12.
Cope et al., "Characterization of the Moraxella catarrhalis uspA1 and uspA2 Genes and Their Encoded Products," Journal of Bacteriology, vol. 181, No. 13, Jul. 1999, pp. 4026-4034 (Total 10 pages).
Corthésy et al., "A Pathogen-specific Epitope Inserted into Recombinant Secretory Immunoglobulin A Is Immunogenic by the Oral Route," The Journal of Biological Chemistry, vol. 271, No. 52, Dec. 27, 1996, pp. 33670-33677.
Corthésy et al., "In vitro assembly of secretory immunoglobulin A (sIgA) from IgA and recombinant secretory component," Journal of Cellular Biochemistry, Jan. 5, 1995, p. 244, abstract only.

(56) References Cited

OTHER PUBLICATIONS

Corthesy et al., "Molecular Definition of the Role of Secretory Component in Secretory IgA-Mediated Protection at Mucosal Surfaces," Journal of Allergy and Clinical Immunology, vol. 109, No. 1, Jan. 1, 2002, p. S113, abstract only.

Corthésy et al., "Secretory Immunoglobulin A: from Mucosal Protection to Vaccine Development," Biological Chemistry, vol. 380, Nov. 1999, pp. 1251-1262.

Corthésy, "Recombinant immunoglobulin A: powerful tools for fundamental and applied research," Trends in Biotechnology, vol. 20, No. 2, Feb. 2002, pp. 65-71.

Corthésy, "Recombinant Secretory Immunoglobulin A in Passive Immunotherapy: Linking Immunology and Biotechnology," Current Pharmaceutical Biotechnology, vol. 4, 2003, pp. 51-67 (Total 18 pages).

Corthésy, "Role of secretory immunoglobulin A and secretory component in the protection of mucosal surfaces," Future Microbiology, vol. 5, No. 5, 2010, pp. 817-829 (Total 14 pages).

Cottet et al., "Microaerophilic Conditions Permit to Mimic in Vitro Events Occurring during in Vivo Helicobacter pylori Infection and to Identify Rho/Ras-associated Proteins in Cellular Signaling," The Journal of Biological Chemistry, vol. 277, No. 37, Sep. 13, 2002, pp. 33978-33986 (10 pages).

Crottet et al., "Mapping the Interaction Between Murine IgA and Murine Secretory Component Carrying Epitope Substitutions Reveals a Role of Domains II and III in Covalent Binding to IgA," The Journal of Biological Chemistry, vol. 274, No. 44, Oct. 29, 1999, pp. 31456-31462 (Total 8 pages).

Crottet et al., "Secretory Component Delays the Conversion of Secretory IgA into Antigen-Binding Competent F(ab')2: A Possible Implication for Mucosal Defense," The Journal of Immunology, vol. 161, 1998, pp. 5445-5453 (Total 10 pages).

Dallas et al., "Binding of Clostridium difficile toxin A to human milk secretory component", J. Med. Microbiol., vol. 47, 1998, pp. 879-888.

Denève et al., "New trends in Clostridium difficile virulence and pathogenesis", International Journal of Antimicrobial Agents, vol. 33, No. S1, 2009, pp. S24-S28.

Deshmane et al., "Monocyte Chemoattractant Protein-1 (MCP-1): An Overview," Journal of Interferon and Cytokine Research, vol. 29, No. 6, 2009, pp. 313-326.

Dewhirst et al., "The Human Oral Microbiome," Journal of Bacteriology, vol. 192, No. 19, Oct. 2010 (Published ahead of print on Jul. 23, 2010), pp. 5002-5017 (Total 17 pages).

Donnelly et al., "Antimicrobial therapy to prevent or treat oral mucositis," The Lancet Infectious Diseases, vol. 3, Jul. 2003, pp. 405-412.

Eldika et al., "Role of nontypeable Haemophilus Influenzae in exacerbations and progression of chronic obstructive pulmonary disease," Current Opinion in Pulmonary Medicine, vol. 12, 2006, pp. 118-124.

Elting et al., "The Burdens of Cancer Therapy: Clinical and Economic Outcomes of Chemotherapy-Induced Mucositis," Cancer, vol. 98, No. 7, Oct. 1, 2003, pp. 1531-1539.

Ertugrul et al., "Comparison of CCL28, interleukin-8, interleukin-1 β and tumor necrosis factor-alpha in subjects with gingivitis, chronic periodontitis and generalized aggressive periodontitis," Journal of Periodontal Research, vol. 48, 2013, pp. 44-51.

European Communication Pursuant to Article 94(3) EPC issued Apr. 23, 2014, in European Patent Application No. 11794757.2.

European Communication Pursuant to Article 94(3) EPC issued Dec. 15, 2014, in European Patent Application No. 11794757.2.

Extended European Search Report dated Aug. 8, 2012, for European Application No. 12158931.1.

Extended European Search Report for European Application No. 10194942.8 dated Oct. 28, 2011.

Extended European Search Report for European Application No. 12158939.4, dated Aug. 17, 2012.

Extended European Search Report, dated Aug. 29, 2012, for European Application No. 12158933.7.

Favre et al., "Simplified procedure to recover recombinant antigenized secretory IgA to be used as a vaccine vector," Journal of Chromatography B, vol. 786, 2003, pp. 143-151 (Total 10 pages).

Gastmeier et al., "Surveillance of Clostridium difficile-associated diarrhoea with the German nosocomial infection surveillance system KISS (CDAD-KISS)", International Journal of Antimicrobial Agents, vol. 33, No. S1, 2009, pp. S19-S23.

Gerding, "Clostridium difficile 30 years on: what has, or has not, changed and why?", International Journal of Antimicrobial Agents, vol. 33, No. S1, 2009, pp. S2-S8.

Gorkiewicz, "Nosocomial and antibiotic-associated diarrhoea caused by organisms other than Clostridium difficile", International Journal of Antimicrobial Agents, vol. 33, No. S1, 2009, pp. S37-S41.

Heiniger et al., "A Reservoir of Moraxella catarrhalis in Human Pharyngeal Lymphoid Tissue," The Journal of Infectious Diseases, vol. 196, Oct. 1, 2007 (Electronically published Aug. 30, 2007), pp. 1080-1087.

Helminen et al., "A Large, Antigenically Conserved Protein on the Surface of Moraxella catarrhalis Is a Target for Protective Antibodies," The Journal of Infectious Diseases, vol. 170, Oct. 1994, pp. 867-872.

Helminen et al., "A Major Outer Membrane Protein of Moraxella catarrhalis Is a Target for Antibodies That Enhance Pulmonary Clearance of the Pathogen in an Animal Model," Infection and Immunity, vol. 61, No. 5, May 1993, pp. 2003-2010 (Total 9 pages).

Hendrickson et al., "Lack of Association of Secretory Component with IgA in J Chain-Deficient Mice," The Journal of Immunology, vol. 157, 1996, pp. 750-754 (Total 6 pages).

Hu et al., "Prospective Derivation and Validation of a Clinical Prediction Rule for Recurrent Clostridium difficile Infection", Gastroenterology, vol. 136, No. 4, Apr. 2009, pp. 1206-1214.

International Preliminary Report on Patentability and Written Opinion of the International Searching Authority (Forms PCT/IB/326, PCT/IB/373 and PCT/ISA/237), dated Sep. 18, 2014, for International Application No. PCT/EP2013/054701.

International Preliminary Report on Patentability and Written Opinion of the International Searching Authority dated Sep. 18, 2014, in PCT International Application No. PCT/EP2013/054697.

International Preliminary Report on Patentability issued in PCT Application No. PCT/EP2013/054722 dated Sep. 18, 2014.

International Search Report and Written Opinion of the International Searching Authority (Forms PCT/ISA/220, PCT/ISA/210 and PCT/ISA/237) for International Application No. PCT/EP2011/072711 dated May 16, 2012.

International Search Report and Written Opinion of the International Searching Authority (Forms PCT/ISA/220, PCT/ISA/210, and PCT/ISA/237) for International Application No. PCT/EP2013/054722, dated May 7, 2013.

International Search Report and Written Opinion of the International Searching Authority (Forms PCT/ISA/220, PCT/ISA/237 and PCT/ISA/210), dated Jun. 17, 2013, for International Application No. PCT/EP2013/054701.

International Search Report and Written Opinion of the International Searching Authority, dated Apr. 18, 2013, for International Application No. PCT/EP2013/054697.

Johnson, "Recurrent Clostridium difficile infection: causality and therapeutic approaches", International Journal of Antimicrobial Agents, vol. 33, No. S1, 2009, pp. S33-S36.

Joost et al., "Characterisation of Clostridium difficile isolates by slpA and tcdC gene sequencing", International Journal of Antimicrobial Agents, vol. 33, No. S1, 2009, pp. S13-S18.

Kanamaru et al., "IgA Fc receptor I signals apoptosis through the FcRy ITAM and affects tumor growth," Blood, vol. 109, No. 1, Jan. 1, 2007 (Prepublished online: Sep. 21, 2006), pp. 203-211 (Total 10 pages).

Kelly et al., "Clostridium difficile—More Difficult Than Ever", The New England Journal of Medicine, vol. 359, No. 18, Oct. 30, 2008, pp. 1932-1940.

Krajci et al., "Molecular Cloning of the Human Transmembrane Secretory Component (POLY-Ig Receptor) and its mRNA Expression in Human Tissues," Biochem. Biophys. Res. Comm., vol. 158, No. 3, Feb. 15, 1989, pp. 783-789.

(56) References Cited

OTHER PUBLICATIONS

Kuijper et al., "Emergence of Clostridium difficile-associated disease in North America and Europe", Clinical Microbiology and Infection, vol. 12, Supplement 6, 2006, pp. 2-18.
Kunisawa et al., "A marvel of mucosal T cells and secretory antibodies for the creation of first lines of defense," CMLS Cellular and Molecular Life Sciences, vol. 62, 2005, pp. 1308-1321.
Liu et al., "CXCL10/IP-10 in infectious diseases pathogenesis and potential therapeutic implications," Cytokine & Growth Factor Reviews, vol. 22, 2011 (Available online Jul. 29, 2011), pp. 121-130.
Lowy et al., "Treatment with Monoclonal Antibodies against Clostridium difficile Toxins", The New England Journal of Medicine, vol. 362, No. 3, Jan. 21, 2010, pp. 197-205.
Lüllau et al., "Antigen Binding Properties of Purified Immunoglobulin A and Reconstituted Secretory Immunoglobulin A Antibodies," The Journal of Biological Chemistry, vol. 271, No. 27, Jul. 5, 1996, pp. 16300-16309.
MacPherson et al., "The immune geography of IgA induction and function," Mucosal Immunology, vol. 1, No. 1, Jan. 2008, pp. 11-22.
Meier et al., "Moraxella catarrhalis strains with reduced expression of the UspA outer membrane proteins belong to a distinct subpopulation," Vaccine, vol. 23, 2005 (Available online Nov. 10, 2004), pp. 2000-2008.
Meier et al., "Salivary Antibodies Directed against Outer Membrane Proteins of Moraxella catarrhalis in Healthy Adults," Infection and Immunity, vol. 71, No. 12, Dec. 2003, pp. 6793-6798 (Total 7 pages).
Merrigan et al., "New approach to the management of Clostridium difficile infection: colonisation with non-toxigenic C. difficile during daily ampicillin or ceftriaxone administration", International Journal of Antimicrobial Agents, vol. 33, No. S1, 2009, pp. S46-S50.
Miller et al., "Comparison of the Burdens of Hospital-Onset, Healthcare Facility-Associated Clostridium difficile Infection and of Healthcare-Associated Infection due to Methicillin-Resistant . . . ", Infection Control and Hospital Epidemiology, vol. 32, No. 4, Apr. 2011, pp. 387-390.
Monteiro et al., "IgA Fc Receptors," The Annual Review of Immunology, vol. 21, 2003 (First published online as a Review in Advance on Jan. 28, 2003), pp. 177-204 (Total 34 pages).
Mose et al., "Can Prophylactic Application of Immunoglobulin Decrease Radiotherapy-Induced Oral Mucositis?" American Journal of Clinical Oncology, vol. 20, Issue 4, Aug. 1997, pp. 407-411 (enlarged copies of the tables included).
Moura et al., "Identification of the Transferrin Receptor as a Novel Immunoglobulin (Ig)A1 Receptor and Its Enhanced Expression on Mesangial Cells in IgA Nephropathy," The Journal of Experimental Medicine, vol. 194, No. 4, Aug. 20, 2001, pp. 417-425.
Murphy et al., "Isolation of the outer membrane of Branhamella catarrhalis," Microbial Pathogenesis, vol. 6, 1989, pp. 159-174.
Nicoletti et al., "A rapid and simple method for measuring thymocyte apoptosis by propidium iodide staining and flow cytometry," J. Immunol. Methods, vol. 139, 1991, pp. 271-279.
Oral Cancer Foundation, "Prevention and Treatment of Oral Mucositis in Cancer Patients," Best Practice, Evidence Based Practice Information Sheets for Health Professionals, vol. 2, Issue 3, 1998, pp. 1-6 (2 pages provided).
Pasquier et al., "Identification of FcαRI as an Inhibitory Receptor that Controls Inflammation: Dual Role of FcRγ ITAM," Immunity, vol. 22, Jan. 2005, pp. 31-42.
Phalipon et al., "Novel functions of the polymeric Ig receptor: well beyond transport of immunoglobulins," Trends in Immunology, vol. 24, No. 2, Feb. 2003, pp. 55-58.
Phalipon et al., "Secretory Component: A New Role in Secretory IgA-Mediated Immune Exclusion In Vivo", Immunity, vol. 17, Jul. 2002, pp. 107-115, XP009107491.
Pituch, "Clostridium difficile is no longer just a nosocomial infection or an infection of adults", International Journal of Antimicrobial Agents, vol. 33, No. S1, 2009, pp. S42-S45.

Pleass et al., "Identification of Residues in the CH2/CH3 Domain Interface of IgA Essential for Interaction with the Human FcαReceptor (Fc αR) CD89," J. Biol. Chem, vol. 274, No. 33, Aug. 13, 1999, pp. 23508-23514 (Total 9 pages).
Plevová et al., "Intravenous Immunoglobulin as Prophylaxis of Chemotherapy-Induced Oral Mucositis," Correspondence, Journal of the National Cancer Institute, vol. 89, No. 4, Feb. 19, 1997, pp. 326-327, XP002680345.
Ponka et al., "The transferrin receptor: role in health and disease," The International Journal of Biochemistry & Cell Biology, vol. 31, 1999, pp. 1111-1137.
Que et al., "Fibrinogen and fibronectin binding cooperate for valve infection and invasion in Staphylococcus aureus experimental endocarditis," The Journal of Experimental Medicine, vol. 201, No. 10, May 16, 2005, pp. 1627-1635.
Ratner et al., "Synergistic proinflammatory responses induced by polymicrobial colonization of epithelial surfaces," Proceedings of the National Academy of Sciences, vol. 102, No. 9, Mar. 1, 2005, pp. 3429-3434.
Rincon, "Interleukin-6: from an inflammatory marker to a target for inflammatory diseases," Trends in Immunology, vol. 33, No. 11, Nov. 2012, pp. 571-577.
Rindisbacher et al., "Production of Human Secretory Component with Dimeric IgA Binding Capacity Using Viral Expression Systems," The Journal of Biological Chemistry, vol. 270, No. 23, Jun. 9, 1995, pp. 14220-14228 (Total 10 pages).
Rodloff et al., "Introduction", International Journal of Antimicrobial Agents, vol. 33, No. 1, 2009, pp. S1-S56 (p. S1 only provided).
Ryu et al., "Therapeutic Effects of Recombinant Human Epidermal Growth Factor (rhEGF) in a Murine Model of Concurrent Chemo- and Radiotherapy-Induced Oral Mucositis," Journal of Radiation Research, vol. 51, 2010, pp. 595-601.
Salamone et al., "Promotion of Neutrophil Apoptosis by TNF-α1," J. Immunol, vol. 166, 2001, pp. 3476-3483.
Schedler et al., "Treatment of radiogenic mucositis in patients with head and neck tumors with polyvalent intramuscular immunoglobulin," Tumor Diagnostik und Therapie, vol. 15, No. 5, 1994, pp. 184-191,XP009161354, along with an English summary.
Schettini et al., "Stimulation of neutrophil apoptosis by immobilized IgA," Journal of Leukocyte Biology, vol. 72, Oct. 2002, pp. 685-691.
Singapore Invitation to Respond to Written Opinion issued Oct. 30, 2014, in Singapore Patent Application No. 2013041322.
Sonis, "Mucositis as a biological process: a new hypothesis for the development of chemotherapy-induced stomatotoxicity," Oral Oncology, vol. 34, 1998, pp. 39-43.
Sonis, "Mucositis: The impact, biology and therapeutic opportunities of oral mucositis," Oral Oncology, vol. 45, 2009 (Available online Oct. 13, 2009), pp. 1015-1020.
Spaniol et al., "Outer membrane protein UspA1 and lipooligosaccharide are involved in invasion of human epithelial cells by Moraxella catarrhalis," Microbes and Infection, vol. 10, 2008 (Available online Oct. 2, 2007), pp. 3-11.
Spielberger et al., "Palifermin for Oral Mucositis after Intensive Therapy for Hematologic Cancers," The New England Journal of Medicine, vol. 351, No. 25, Dec. 16, 2004, pp. 2590-2598.
Stokman et al., "Oral mucositis and selective elimination of oral flora in head and neck cancer patients receiving radiotherapy: a double-blind randomised clinical trial," British Journal of Cancer, vol. 88, No. 7. 2003, pp. 1012-1016.
Surawicz et al., "Treatment of refractory and recurrent Clostridium difficile infection", Nature Reviews, vol. 8, Jun. 2011 (published online Apr. 19, 2011), pp. 330-339.
Suzuki et al., "Autocrine production of epithelial cell-derived neutrophil attractant-78 induced by granulocyte colony-stimulating factor in neutrophils," Blood, vol. 99, No. 5, Mar. 1, 2002, pp. 1863-1865.
Takeshita et al., "Intravenous immunoglobulin preparations promote apoptosis in lipopolysaccharide-stimulated neutrophils via an oxygen-dependent pathway in vitro," APMIS, vol. 113, 2005, pp. 269-277.

(56) References Cited

OTHER PUBLICATIONS

The Human Microbiome Project Consortium, "Structure, function and diversity of the healthy human microbiome," Nature, vol. 486, Jun. 14, 2012, pp. 207-214.

Van Der Steen et al., "Immunoglobulin A: FcαRI Interactions Induce Neutrophil Migration Through Release of Leukotriene B4," Basic-Alimentary Tract, Gastrogenterology, vol. 137, No. 6, Dec. 2009, pp. 2018-2029.e3.

Von Gunten et al., "Siglec-9 transduces apoptotic and nonapoptotic death signals into neutrophils depending on the proinflammatory cytokine environment," Blood, vol. 106, No. 4, Aug. 15, 2005 (Prepublished online: Apr. 12, 2005), pp. 1423-1431 (Total 10 pages).

Watkins et al., "Attenuation of radiation- and chemoradiation-induced mucositis using gamma-D-glutamyl-L-tryptophan (SCV-07)," Oral Diseases, vol. 16, 2010, pp. 655-660.

Weiss, "Clostridium difficile and fluoroquinolones: is there a link?", International Journal of Antimicrobial Agents, vol. 33, No. S1, 2009, pp. S29-S32.

Wheeler et al., "Immune Components of Colostrum and Milk—A Historical Perspective," Journal of Mammary Gland Biological Neoplasia, vol. 12, 2007 (Published online Nov. 9, 2007), pp. 237-247 (Total 12 pages).

Wijers et al., "Mucositis reduction by selective elimination of oral flora in irradiated cancers of the head and neck: A placebo-controlled double-blind randomized study," International Journal of Radiation Oncology Biology Physics, vol. 50, No. 2, 2001, pp. 343-352.

Wörn et al., "Stability Engineering of Antibody Single-chain Fv Fragments," J. Mol. Biol, vol. 305, 2001, pp. 989-1010.

Zuercher et al., "Plasma-derived immunoglobulins," Principles of Immunopharmacology: 3rd revised and extended edition, 2011, pp. 271-301.

Balsari et al., "Topical Administration of a Doxorubicin-specific Monoclonal Antibody Prevents Drug-induced Mouth Apoptosis in Mice," British Journal of Cancer, vol. 85, No. 12, 2001, pp. 1964-1967.

Bessen et al., "Passive Acquired Mucosal Immunity to Group A Streptococci by Secretory Immunoglobulin A," Journal of Experimental Medicine, vol. 167, No. 6, Jun. 1, 1988, pp. 1945-1950.

Boullier et al., "Secretory IgA-Mediated Neutralization of Shigella flexneri Prevents Intestinal Tissue Destruction by Down-Regulating Inflammatory Circuits," The Journal of Immunology, vol. 183, No. 9, 2009, pp. 5879-5885.

Brandtzaeg, "Role of Secretory Antibodies in the Defence Against Infections," Int J. Med. Microbiol., vol. 293, 2003, pp. 3-15.

Cheng et al., "Evaluation of an Oral Care Protocol Intervention in the Prevention of Chemotherapy-induced Oralnlucositis in Paediatric Cancer Patients," European Journal of Cancer, vol. 37, 2001, pp. 2056-2063.

CSL Behring, "Company Core Data Sheet for Beriglobin," Sep. 16, 2015, together with an English translation thereof, 17 pages total.

De Wit et al., "Structure of the gene for the human myeloid IgA Fc receptor (CD89)," The Journal of Immunology, vol. 155, 1995, pp. 1203-1209 (Total 8 pages).

Delacroix et al., "Changes in Size, Subclass, and Metabolic Properties of Serum Immunoglobulin A in Liver Diseases and in Other Diseases with High Serum Immunoglobulin A," J Clin. Invest., vol. 71, Feb. 1983, pp. 358-367.

Delacroix et al., "Selective Transport of Polymeric Immunoglobulin A in Bile," J Clin. Invest., vol. 70, Aug. 1982, pp. 230-241.

English translation of Russian Office Action, dated Nov. 12, 2015, for Russian Application No. 2013132220.

English translation of the Japanese Office Action, dated Nov. 1, 2016, for corresponding Japanese Application No. 2014-560392.

English translation of the Japanese Office Action, dated Oct. 25, 2016, for Japanese Application No. 2014-560387.

Fluckiger et al., "Immunoglobulins Inhibit Adherence and Internalization of *Streptococcus pyogenes* to Human Pharyngeal Cells," Advances in Experimental Medicine and Biology, vol. 418, 1997, pp. 909-911.

Fluckiger et al., "Immunoglobulins to Group A Streptococcal Surface Molecules Decrease Adherence to and Invasion of Human Pharyngeal Cells," Infection and Immunity, vol. 66, No. 3, Mar. 1998, pp. 974-979.

Frese et al., "Maximizing Mouse Cancer Models," Nature Reviews, vol. 7, Sep. 2007, pp. 645-658.

Gonzalez-Quintela et al., "Serum levels of immunoglobulins (IgG, IgA, IgM) in a general adult population and their relationship with alcohol consumption, smoking and common metabolic abnormalities," Clinical and Experimental Immunology, 2007, vol. 151, pp. 42-50.

Himi et al., "Immune Barrier Changes in Patients with Head and Neck Cancer," Stomato-pharyngology, vol. 6, No. 2, 1994, pp. 71-77, with an English abstract.

Janeway Jr, et al., "Immunobiology," 3rd edition, Garland Publishing Inc., 1997, pp. 8:18-8:19 and 9:19-9:20.

Japanese Office Action for Japanese Application No. 2013-543743 dated Dec. 1, 2015, with an English translation.

Johansen et al., "Role of J Chain in Secretory Immunoglobulin Formation," Scandinavian Journal of Immunology, vol. 52, 2000, pp. 240-248.

Karolewska et al., "Antibacterial potential of saliva in children with leukemia," Oral Surgery, Oral Medicine, Oral Pathology, Oral Radiology, and Endodontics, vol. 105, No. 6, Jun. 2008, pp. 739-744.

Keefe et al., "Updated Clinical Practice Guidelines for the Prevention and Treatment of Mucositis," Cancer, vol. 109, No. 5, Mar. 1, 2007, pp. 820-831.

Leibl et al., "Method for the Isolation of Biologically Active Monomeric Immunoglobulin A from a Plasma Fraction," Journal of Chromatography B, 1996, pp. 173-180.

Lindh et al., "Binding of Secretory Component to Human Immunoglobulin M," Eur. J. Biochem., vol. 62, 1976, pp. 271-278.

Lüer et al., "Topical Curcumin Can Inhibit Deleterious Effects of Upper Respiratory Tract Bacteria on Human Oropharyngeal Cells in Vitro: Potential Rrole for Patients with Cancer Therapy Induced Mucositis?" Support Care Cancer, vol. 19, 2001 (Published online: May 14, 2010), pp. 799-806.

Morelli et al., "Oral Administration of Anti-Doxorubicin Monoclonal Antibody Prevents Chemotherapy-induced Gastrointestinal Toxicity in Mice," The Journal of Cancer Research, vol. 56, May 1, 1996, pp. 2082-2085 (Total 5 pages).

Olson et al., "Effect of Host Defenses on Clostridium difficile toxin-induced Intestinal Barrier Injury," J Trauma Acute Care Surg, vol. 74, No. 4, 2013, pp. 983-990.

Phalipon et al., "Monoclonal Immunoglobulln A Antibody Directed against Serotype-specific Epitope of Shigella Flexneri Lipopolysaccharide Protects against Murine Experimental Shigellosis," J. Exp. Med., vol. 182, Sep. 1995, pp. 769-778.

Prinsloo et al., "In Vitro Refolding of Recombinant Human Free Secretory Component Using Equilibrium Gradient Dialysis," Protein Expression and Purification, vol. 47, 2006 (Available online Oct. 21, 2005), pp. 179-185.

Saito et al., "Biological Activity of Secretory IgA, Particularly antibacterial immunity as an example," J. Stomatol. Soc. Jpn., Apr. 26, 1976, vol. 43, No. 2, pp. 107-112.

Sørensen et al., "Structural requirements for incorporation of J chain into human IgM and IgA," International Immunology, vol. 12, No. 1, 2000, pp. 19-27.

Steinbuch et al. "Isolement de L'Immunoglobuline IgG Du Plasma Humain a L'Aide de L'Acide Caprylique," Rev. Franc. Etudes Clin. et Biol., vol. XIV, 1969, pp. 1054-1058, with English abstract on p. 1057.

Wright et al, "Neutrophil Function in Inflammation and Inflammatory Diseases," Rheumatology, vol. 49, 2010 (Advanced Access publication Mar. 24, 2010), pp. 1618-1631.

(56) References Cited

OTHER PUBLICATIONS

Stubbe et al., "Polymeric IgA is Superior to Monomeric IgA and IgG Carrying the Same Variable Domain in Preventing Clostridium difficle Toxin A Damaging of T84 Monolayers," J Immunol, vol. 164, No. 4, Feb. 15, 2000, pp. 1952-1960.
Third Party Observation for Application No. EP 20130708787 issued on Apr. 7, 2017.
U.S. Office Action issued in U.S. Appl. No. 15/384,140 dated Sep. 14, 2017.

* cited by examiner

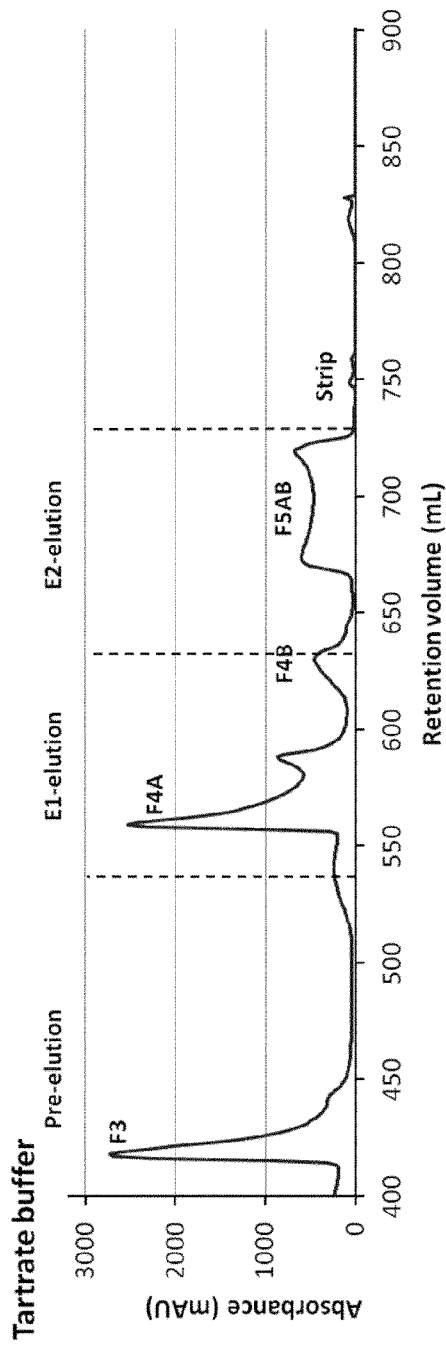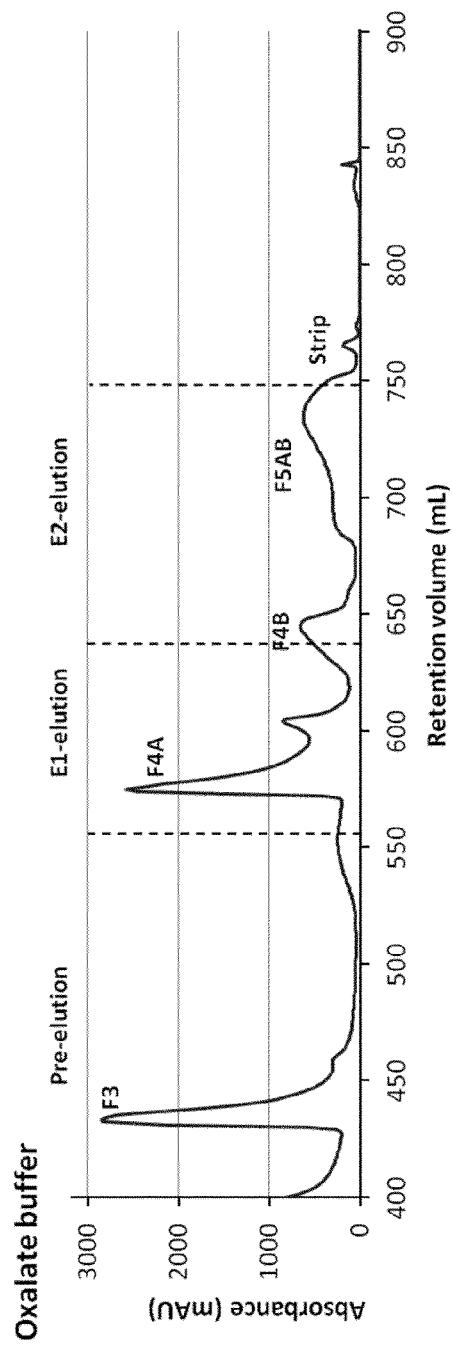

PROCESS FOR ENRICHING IGA

The invention relates to a process for enriching IgA (and IgM) from IgA-comprising material. In particular, it relates to a sequential elution process of an anion exchanger that leads to an advantageous enrichment and separation of monomeric and dimeric IgA.

INTRODUCTION

As is well known, immunoglobulins play an important role in the immune system of mammals in fighting infections. Immunoglobulins (Ig) are specific immune proteins synthesized by B-lymphocytes, found in blood plasma, lymph and other body secretions of all vertebrates. Immunoglobulins constitute approximately 20% of the plasma proteins in humans.

All immunoglobulins, independent of their specificity, have a common structure with four polypeptide chains: two identical heavy (H) chains, each carrying covalently attached oligosaccharide groups, and two identical, usually non-glycosylated light (L) chains; the chains are linked covalently by disulphide bonds. All four polypeptide chains contain constant (C) and variable (V) regions, found at the carboxyl and amino terminals, respectively. Heavy and light chains have a single V region, while light chains possess a single C region and heavy chains contain three C regions. The V regions of both heavy and light chains combine to form two identical antigen binding sites (the parts of the antibody which bind to the antigen). Structural determinants within the Fc region of the immunoglobulin mediate effector functions such as placental transport or antigen-dependent cellular toxicity.

Immunoglobulins are divided according to their H chain components into five major classes with differing biochemical and physiological properties: IgG (γ heavy chain), IgA (α), IgM (μ), IgD (δ) and IgE (ε). There are two types of light chain, κ and λ. Individual molecules may contain κ or λ chains but never both. In man, the ratio of immunoglobulins containing κ or λ light chains is about 60:40.

Due to the availability and range of applications, three immunoglobulin classes, IgG, IgA and IgM, are more important than the others. Human IgG represents the most abundant immunoglobulin in plasma, whereas IgA represents the main antibody class in external secretions such as saliva, tears and mucus of the respiratory and intestinal tracts. IgA forms one of the first lines of defense against bacterial and viral pathogens. IgM is by far the physically largest antibody in the human circulatory system, appears early in the course of an infection and usually reappears, to a lesser extent, after further exposure.

The pure monomeric form of IgA consists of two light (L) and two heavy (H) chains; in the true dimeric form, two such monomers are coupled by a so-called J chain (joining chain). In plasma, IgA monomers exist in an equilibrium with non-covalently associated IgA dimers; however, J chain-containing IgA dimers are also present. Total dimeric IgA (i.e. J chain-containing true dimers and non-covalently associated IgA dimers) constitutes approximately 10-25% of total IgA. In the secretions of the mucous membranes and glands, J-chain containing IgA dimers with an additional secretory component (SC) are predominant. There are two sub-classes of IgA, IgA1 and IgA2 which are normally present in human serum in a relative proportion of about 80-90% to 10-20% by weight. This relationship can be altered during IgA isolation. The natural ratio of κ to λ light chains in an immunoglobulin preparation amounts to approximately 1:1. IgA only represents approximately 3-4% of the total protein of normal human serum.

IgM forms polymers where multiple monomers are covalently linked together with disulfide bonds, mostly as a pentamer but also as a hexamer. The J chain is found in pentameric IgM but not in the hexameric form, perhaps due to space constraints in the hexameric complex. Pentameric IgM can also be made in the absence of J chain. At present, it is still uncertain what fraction of normal pentamer contains J chain, and to this extent it is also uncertain whether a J chain-containing pentamer contains one or more than one J chain (Erik J. Wiersma et al. (1998) J. Immunol. 160: 5979-5989). Because IgM is a large molecule; it cannot diffuse well, and is found in the interstitium only in very low quantities. IgM is primarily found in serum, but because of the presence of the J chain, it is also important as a secretory immunoglobulin. Due to its polymeric nature, IgM possesses high avidity, and is particularly effective for complement activation.

During the last century, immunoglobulin preparations were successfully used for the prophylaxis and treatment of various infectious diseases. Traditionally, immunoglobulin preparations were developed for systemic administration, and were largely comprised of IgG. However, the successful use of breast milk for the prophylaxis and treatment of infant diarrhoea highlighted the potential benefits of plasmatic and mucosal (secretory) IgA (Hammarstrom L. et al. (1994) Immunol. Rev. 139: 43-70).

A clinical trial conducted by Eibl et al (Eibl, M. et al. (1988) N Engl J Med 319: 1-7) indicates that oral-feeding with a plasma derived IgA-rich immunoglobulin preparation (IgAbulin 73% IgA and 26% IgG) may prevent the development of necrotizing enterocolitis. Other indications, e.g. indications involving mucosal infections, may also benefit from treatment with IgA. However, IgAbulin is no longer available, and presently no IgA-product is available.

The known and common methods for isolation and purification of immunoglobulins are mostly based on differences in physicochemical and biological properties of molecules belonging to this group, such as their molecular masses, isoelectric points, solubility under different conditions; in addition, their affinity to some substances (e.g. bacterial A- and G-proteins) must be taken into consideration. Gel chromatography, affinity chromatography and ion exchange chromatography, dialysis, precipitation by salts and organic solvents are based on different properties of immunoglobulin molecules. The most widely used protocols described in the literature combine several approaches.

Commercial processes for the isolation of immunoglobulins from plasma pools usually start with ethanol fractionation, e.g. as developed by Cohn (Cohn et al. (1946) J. Am. Chem. Soc. 68, 459; Oncley et al. (1949), J. Am. Chem. Soc. 71, 541). Numerous variants of the original Cohn process have been described.

An alternative approach to ethanol precipitation is described by Steinbuch et al. (Rev. Franc. Et. Clin. et Biol. 1969, XIV, 1054). This approach uses octanoic acid for precipitation leaving immunoglobulins in the supernatant. The immunoglobulins are further purified by adsorption (in "batches") using an anion exchanger, DEAE-cellulose.

The use of chromatographic methods for the purification of IgG from immunoglobulin-rich plasma fractions for IVIG products has already been explored. In particular, cation and anion exchange chromatography in separate steps or in series are described in patented methods for the purification of IgG from plasma or fractions thereof. In the majority of the patented methods, anion exchange chromatography is used in negative mode, i.e. conditions are used to enable the binding of the contaminating proteins, e.g. IgA, IgM, albumin, fibrinogen, transferrin, while IgG is in the non-adsorbed product. IgA and IgM can be eluted from the anion exchange column e.g. by increasing the ion strength.

In addition, various chromatographic separation processes have been developed to increase the purity of the products. Those yielding the best performance (in particular EP 0 703 922, WO 99/64462) include at least two successive chromatography steps, one using anion exchange and the other using cation exchange. The specificity of these processes is provided by the property of the anion exchangers of not adsorbing the IgG, under conventional conditions of implementation, but of binding most of the other proteins co-purified during the pre-purification steps.

In U.S. Pat. No. 6,307,028 B1 for the purification of IgG from plasma or fractions thereof, e.g. Cohn fractions II+III, there are two chromatographic steps after pretreatment with caprylic acid. In the first step, a strong anion exchanger is used to bind IgA; in the second step, a weak anion exchanger is used to bind the IgM. The inventors claim that they could elute IgA and IgM, respectively, with high salt.

Although numerous IgA fractionation methods have been described in the literature, surprisingly few IgA immunotherapy products have been marketed by the pharmaceutical industry. It seems that the availability of IgA for immunotherapeutic use has been limited by technical constraints. Methods for large scale fractionation of IgA fail to produce a highly purified preparation (i. e. greater than 90%), and small scale purification methods (e. g. anti-IgA affinity columns) cannot provide a commercially viable product. Accordingly, methods for large scale purification of IgA, which generate highly purified IgA preparations suitable for immunotherapeutic use, are desirable. In particular, IgA free of IgG is highly desirable due to the fact that IgG may adversely affect the anti-inflammatory properties of IgA.

IgA can be fractionated from plasma or other biological fluid using various combinations of precipitations, including ammonium sulfate, ethanol, caprylic acid, polyethylene glycol, and chromatographic techniques. Chromatography resins used to isolate IgA include DEAE cellulose, Sephadex G-200, DEAE-Sephadex A-50, affinity chromatography on anti-IgG and anti-IgM immunosorbents, Jacalin-Sepharose, Protein G-Sepharose, Fastflow-S Sepharose, Superose 6, thiophilic adsorption, Sephacryl S-300, anti-IgA antibody conjugated to cyanogen bromide-activated Sepharose 4B, protein-A and protein-G affinity chromatography (Cripps, A. W. et al. (1983) J. Immunol. Methods 57: 197-204; Doellgast, D. J. et al. (1976) Immunochemistry. 13: 135-139; Kobayashi, K. et al. (1987) Adv. Exp. Med. Biol. 216B: 1193-1197; Leibl, H. et al. (1995) Protein Expression and Purification 6: 408-410; Pejaudier, L. et al. (1972) Vox. Sang. 23: 165-175; Roque-Barriera, M. et al. (1985) J. Immunol. 134: 1740-1743). However, none of these techniques have so far provided a large-scale purification process that makes it commercially viable to purify IgA from plasma or other IgA-comprising materials.

WO 97/25352 describes a method to separate the immunoglobulins IgG and IgA in an immunoglobulin-containing starting material from each other and also from their high molecular aggregates as well as from other high molecular contaminating substances which were either already present in the starting material or were formed during the purification steps using hydroxylapatite, especially ceramic hydroxylapatite and further purification steps. While the process described in this patent application is suitable for large scale production of IgA-comprising solutions, it has several disadvantages that make it desirable to develop an improved process. For example, the material used as starting material is Cohn Fraction III obtained from Fraction II+III which means that this fraction then cannot be used for IgG production, making commercially less attractive. In addition, the resulting IgA solution requires several further purification steps (chromatography) to achieve a preparation of an acceptable purity.

The applicant has therefore developed a new chromatographic process for the preparation of immunoglobulin A and M from an IgA-comprising composition and/or immunoglobulin-containing material. Advantageously, side fractions and/or waste material that are obtained during the process for the purification and isolation of IgG can be used for the isolation and purification of IgA (and IgM).

The new method offers several advantages compared to other methods described in literature. This method is characterised by a simple sequential and selective elution without salt gradients. The use of dicarboxylic acids and/or dihydroxy-dicarboxylic as well as hydroxy-tricarboxylic acids (or salts thereof) in weakly acidic to slightly alkaline conditions allows a highly competitive action against the charged surface of the anion exchange resin. In addition, the pH remains constant during the elution of the respective peak fractions. In addition, the pH of the elution buffers stays constant.

The process can separate the immunoglobulins into subfractions, which can serve as starting material for producing highly pure IgA and IgM concentrates. In addition, the process results in an enrichment of monomeric and dimeric/polymeric immunoglobulins in separate subfractions. By this method it is possible to produce several useful concentrates of immunoglobulins by a single ion exchange chromatography step, which can then be further processed to yield compositions enriched in monomeric IgA, or dimeric IgA as desired. Advantageously, the described method provides significant improvements over current state of the art purification methods for the preparation of highly pure IgA.

SUMMARY OF THE INVENTION

One aspect of the invention is therefore a method for enriching IgA from an IgA-comprising composition, comprising the following steps:
(a) loading the composition onto an anion exchanger under conditions that allow the IgA to bind,
(b) applying an alkaline elution solution comprising a substance with at least 2 acid groups,
wherein protein eluted during step b is enriched for monomeric IgA.

Preferably, a pre-elution step (a1) is carried out between steps (a) and (b) by applying a low conductivity solution to the anion exchanger. Preferably, this step (a1) is performed at a weakly acidic to neutral pH.

Preferably, the substance in step (b) is selected from a multivalent carboxylic acid or a multivalent hydroxy-carboxylic acid or salts thereof, and/or phosphate, more preferably, the substance is selected from a dihydroxy-dicarboxylic and/or dicarboxylic acid or salt thereof such as tartaric acid/tartrate, oxalic acid/oxalate, maleic acid/maleate, malonic acid/malonate, a hydroxy-tricarboxylic acid or salt thereof such as citric acid/citrate, and/or phosphate. The dihydroxy-dicarboxylic acid or salt thereof is preferably selected from tartaric acid/tartrate, oxalic acid/oxalate, malonic acid/malonate, and maleic acid/maleate. More preferably, the dihydroxy-dicarboxylic acid or salt thereof is tartaric acid/tartrate or oxalic acid/oxalate. In a preferred embodiment the pH of the alkaline solution in step (b) is stabilized by addition of an additional buffer component, preferably Tris buffer at pH 7.6±0.4, to a final concentration of 1 to 20 mM, preferably 2 to 15 mM, more preferably 5 to 10 mM.

Preferably, the eluate collected during step b is essentially devoid of IgM.

Another aspect of the invention is the method described above, with an additional (optional) step (c), a further elution step carried out by applying an acidic elution solution that comprises a strong competitor for the anion exchanger. Preferably, the protein eluted in step c is enriched in dimeric IgA.

Preferably, the strong competitor for the anion exchanger in step (c) is selected from citrate, benzenesulfonic acid, benzoic acid and salts of hydrogen sulfates or mixtures thereof. More preferably, the strong competitor for the anion exchanger is citrate.

The anion exchanger used in the method of the invention can be a strong anion exchanger or a weak anion exchanger. Preferably, the anion exchanger comprises an anion exchange ligand such as quaternary ammonium, quaternary aminoethyl, diethylaminoethyl, trimethylaminoethly, or dimethylaminoethyl. More preferably, the anion exchanger is selected from MPHQ, DEAE Sepharose FF, Q Sepharose (HP and FF), ANX Sepharose FF (low and high substituted), Capto Q, Capto Q XP, Capto DEAE, Capto ANX, Macro Cap Q, Source 30 Q and 15 Q, Q Hyper Cel, Giga Cap Q 650M, QAE 550 C, DEAE Biogel A, Fractogel DEAE, Fractogel TMAE and Fractogel DMAE.

Preferably, the IgA-comprising composition is or is derived from blood, serum, plasma or other biological fluids. More preferably, the IgA-comprising composition is an intermediate or a side fraction obtained during plasma fractionation or purification of IgG from plasma.

In a preferred aspect of the invention, the IgA-comprising composition is an intermediate in an IgG purification process, and the anion exchanger used in the method of the invention is part of the IgG production process. The IgG will be mainly found in the flow-through of the anion exchanger, whereas the IgA is eluted according to the methods described above.

In another preferred aspect of the invention, the IgA-comprising composition is obtained by solubilising a precipitate. Preferably, the precipitate is an octanoic acid precipitate obtained during IgG purification. The supernatant of the octanoic acid precipitate is normally processed further to purify IgG. Preferably, the solubilisation step selectively brings IgA and IgG into solution. Preferably, the solubilisation is carried out using a solution with a conductivity of between 1 and 15 mS/cm, and a pH of 3.5 to 6 or 7 to 9.5. More preferably, the solubilisation is carried out with a phosphate buffer, an acetate buffer, a Tris buffer, and/or a combination of two or more of these buffers. Even more preferably, the buffer is selected from 0.22 M acetate buffer or 0.15 M phosphate buffer, pH 4.8.

Preferably, the buffer and intermediate precipitate are used at a ratio of between 1:5 to 1:12.

Another aspect of the invention is the use of anion exchange chromatography to separate monomeric and dimeric IgA by sequential elution.

DETAILED DESCRIPTION OF THE INVENTION

The present invention concerns an improved method for preparing an IgA enriched fraction, from an IgA-comprising composition. From the fraction obtained with the method of the invention, highly pure IgA concentrate can be produced for therapeutic use. The method comprises a single anion exchange chromatography step carried out at slightly acidic to neutral pH, thereby enabling IgA to be retained on the chromatographic support, while most of the IgG is collected in the flow through in a relatively pure form. Afterwards, retained IgA and other contaminants are fractionated using sequential, selective elution at slightly acidic to alkaline pH. The invention also relates to a chromatographic process for the separation of monomeric and dimeric IgA.

The IgA-comprising composition can be any material, preferably a biological fluid, containing IgA. Preferably, the IgA-comprising composition is or is derived from blood, plasma or serum. The IgA-comprising composition can be a solution of a paste or precipitate, preferably fraction (FI+II+III), (FII+III), or FIII, from a cold ethanol fractionation process, e.g. as described in Cohn/Oncley (Cohn et al. (1946) J. Am. Chem. Soc. 68, 459; Oncley et al. (1949), J. Am. Chem. Soc. 71, 541), or precipitate A, precipitate B and precipitate G as described in the Kistler and Nitschman process (H. Nitschmann et al (1954) Helvetica Chimica Acta 37, 866-73), or modifications thereof.

The IgA-comprising composition is preferably a solution of an intermediate precipitate or an intermediate solution or waste fraction obtained during the purification of IgG using octanoic acid-, polyethylene glycol- and/or ammonium sulphate precipitation starting from plasma, or any IgA-comprising intermediate or waste fraction. However, the method using other IgA-containing starting materials is also intended to be included in the invention. For example, IgA can also be enriched from other biological fluids such as milk or saliva using the method of the invention.

Preferably, the starting material is an intermediate solution already enriched with immunoglobulins by upstream process steps, prepared for application to an anion exchanger during a process for purification of IgG from plasma or plasma fractions described above. Preferably, most of the IgG does not bind to the anion exchanger and can be directly processed further for IgG purification. The bound material, comprising the majority of the IgA contained in the intermediate solution, can then be eluted according to the method of the invention.

When a precipitate is used as the starting material, the IgA can be extracted from the precipitate (process fraction or side/waste fraction) by resuspending the precipitate in a buffer for several hours. Preferably, IgA and IgG will be selectively solubilised during the resuspension step. Preferably, the solubilisation is carried out using a solution with a conductivity between 1 and 15 mS/cm, more preferably between 5 and 15 mS/cm. The pH is either between 3.5 and 6, or between 7 and 9.5. If an acidic pH is chosen, it is preferably between 4 and 5.5, more preferably between 4.5 and 5.2, most preferably around 4.8. If an alkaline pH is chosen, it is preferably between 7 and 9, more preferably between 7.5 and 8.5. Preferably, a phosphate buffer, an acetate buffer, or a Tris buffer at a pH of about 4.8 is used, combinations of two or more of these buffers can also be used. More preferably, the solubilisation is carried out with a 0.1 to 0.2M, preferably a 0.15M phosphate buffer, or a 0.1 to 0.3M, preferably 0.2 M acetate buffer at pH 4.8. However, the skilled person will be able to identify further suitable buffers. The ratio of buffer and precipitate is about 1:5 to 1:12, preferably 1:5, 1:7, 1:10 or, 1:12, but other ratios can also be used. The solubilisation is carried out for at least 2 hours, preferably for at least 4 hours, even more preferably overnight, under strong agitation using a suitable mixer (e.g. Vibro mixer from e.g. Graber or Viscoprop from e.g. Ekato).

Optionally, a clarification step may be carried out after the solubilisation, e.g. by depth filtration.

The first step according to the method of the invention is loading the IgA-comprising composition onto an anion exchanger. The anion exchanger can be provided as a column, a membrane, any type of matrix, resin or other base material, and comprises an anion exchange ligand. The method of the invention can be carried out on any type of anion exchanger, a weak, a strong or a mixed mode anion exchanger, as long as it is carried out under conditions enabling the IgA to be retained on the anion exchanger during the loading phase, while the IgG is collected in the flow through in a relatively pure form.

The anion exchange ligand is a positively charged group. For example, an anion exchanger may comprise groups such as quaternary ammonium, quaternary aminoethyl, diethylaminoethyl, trimethylaminoethly, or dimethylaminoethyl as ligands. Examples of suitable anion exchangers are MPHQ, DEAE Sepharose FF, Q Sepharose (HP and FF), ANX Sepharose FF (low and high substituted), Capto Q, Capto Q XP, Capto DEAE, Capto ANX, Macro Cap Q, Source 30 Q and 15 Q, Q Hyper Cel, Giga Cap Q 650M, QAE 550 C, DEAE Biogel A, Fractogel DEAE, Fractogel TMAE and Fractogel DMAE. Most preferred anion exchangers are MPHQ or Fractogel DEAE MD.

The loading is performed under conditions that allow IgA to bind to the anion exchanger (step (a)). Typically, the anion exchanger is equilibrated prior to use, often with a two buffer system (equilibration buffer 1 and 2), whereby the equilibration buffer 2 is used prior to loading. The IgA-comprising solution is usually adjusted to have a similar pH and conductivity as the equilibration buffer (equilibration buffer 2 when using a two buffer system). The equilibration buffers are common buffer systems adapted to the used anion exchanger. The conductivity of the equilibration buffer 1 is between 5 and 50 mS/cm, more preferably between 5 and 45 mS/cm. The pH is between 3 and 8. Examples of suitable buffers are phosphate or acetate buffers or combinations thereof. Preferably, the buffer is an acetate buffer, pH 3 to 5, or phosphate buffer, pH 7 to 8. Most preferred choices for equilibration buffer 1 are about 0.8 M acetate buffer, pH 3.5 to 4.5 with a conductivity of about 8 mS/cm, about 0.5 M phosphate buffer, pH 7 to 8 with a conductivity of about 40 mS/cm or about 0.1 M phosphate buffer, pH 7 to 8 with a conductivity of about 10 mS/cm. The conductivity of the equilibration buffer 2 is between 0.5 and 1.5 mS/cm, more preferably between 0.7 and 1.3 mS/cm. The pH is between 5 and 8.5. Examples of suitable choices for equilibration buffer 2 are phosphate, acetate and combinations thereof. Preferably, the buffer is an acetate buffer, pH 6 to 7 or phosphate/acetate buffer, pH 7-8. Most preferred buffers for equilibration buffer 2 are about 10 mM acetate buffer, pH 6 to 6.6 with a conductivity of about 1 mS/cm, about 7.5 mM phosphate and 2.5 mM acetate buffer, pH 6 to 6.6 with a conductivity of about 1 mS/cm, or about 5 mM phosphate and 10 mM acetate buffer, pH 6 to 6.6 with a conductivity of about 1 mS/cm.

After loading the anion exchanger, it is typically washed with the equilibration buffer 2 to remove any unbound material.

Optionally, a pre-elution step can be performed to remove loosely bound material. This can be done with a buffer containing phosphate, acetate and combinations thereof. In the present invention the pre-elution is preferably carried out with a low conductivity solution, preferably at a weakly acidic or neutral pH. More preferably, a phosphate/acetate buffer is used, preferably at a concentration of about 5 to 15 mM phosphate and 15 to 45 mM acetate, more preferably at about 10 mM phosphate and 30 mM acetate. The pH of the pre-elution buffer is about 6.0 to 6.8, preferably pH of 6.0 is used, but the skilled person will be able to choose other suitable buffers. In the present invention, the pre-elution fraction(s) contain(s) mostly IgG, and the pre-elution is preferably used when the IgA-comprising composition contains a high amount of IgG as compared to the amount of IgA.

After the optional pre-elution step, the buffer is changed to a first elution buffer (step (b)). The inventors have advantageously found that using a multivalent carboxylic or a multivalent hydroxycarboxylic acid, preferably a dihydroxy-dicarboxylic acid or hydroxy-tricarboxylic acid, or salt thereof, produces a good enrichment of IgA, predominantly monomeric IgA, in the material, typically fraction(s), collected during the first elution. Alternatively, a phosphate buffer can be used for this elution step. Preferably, the material collected during the first elution is essentially devoid of IgM. Preferably, an alkaline pH is used, for example a pH between 7.2 and 9.0, more preferably between 7.4 and 7.8, most preferably a pH of about 7.6. Preferably, the dihydroxy-dicarboxylic acid or hydroxy-tricarboxylic acid or salt thereof is selected from tartaric acid/tartrate, oxalic acid/oxalate, malonic acid/malonate, maleic acid/maleate, or citric acid/citrate. Preferably, the first elution buffer contains the multivalent carboxylic or multivalent hydroyx-dicarboxylic acid or salt thereof at a concentration of 5 to 100 mM, more preferably of 20 to 80 mM, even more preferably of 25 to 65 mM, most preferably of about 55 mM. In addition the first elution buffer may contain other buffer substances such as sodium acetate. For example, the first elution solution may contain 1 to 20 mM sodium acetate, preferably 1 to 10 mM sodium acetate, most preferably about 5 mM sodium acetate. Preferably, the first elution solution may comprise an additional buffer component, at pH 7.6±0.4, preferably Tris, to a final concentration of 1 to 20 mM, preferably 2 to 15 mM, more preferably 5-10 mM. The skilled person will be able to choose other substances and suitable concentrations thereof that will be suitable to achieve the desired pH and conductivity of the first elution solution.

More preferably the dihydroxy-dicarboxylic acid or salt thereof in the first elution solution is tartrate or oxalate, most preferably it is tartrate.

Preferably, the material collected during the first elution is enriched in monomeric IgA and essentially free of IgM, i.e. IgM-depleted.

In a more preferred embodiment of the invention, an additional step (c) is carried out, which is a second elution step. The material, typically fraction(s), eluted in step (c) is/are enriched for dimeric IgA, including J-chain-containing IgA. If IgM is present in the IgA-comprising composition, IgM is also likely to elute in this step.

If the second elution step is desired, the buffer will then be changed to the second elution buffer. Preferably, the second elution buffer will contain a strong competitor for the anion exchanger in order to replace the bound protein from the anion exchanger. Examples of such strong competitors are citrate, benzenesulfonic acid, benzoic acid and salts of hydrogen sulfates or mixtures thereof. The most preferred competitor is citrate. Preferably the pH of the second elution buffer will be about 3.0 to 6.0, more preferably about 4.5 to 5.5, most preferably the pH is 5.0. Preferably the concentration of citrate in the second elution buffer is 1 to 100 mM, more preferably 1 to 50 mM, even more preferably about 25 mM. In addition the second elution buffer may contain other buffer substances such as phosphate, preferably concentration is 40 to 50 mM. Most preferably, the second elution buffer may contain 50 mM sodium phosphate and 25 mM citrate at a pH of 5.0.

The material or fractions that are enriched in IgA, or that are enriched in monomeric IgA, or in dimeric IgA as desired, are then pooled as desired and optionally further processed. For example, size exclusion chromatography can be carried out to separate, for example, dimeric IgA from IgM and monomeric IgA, affinity chromatography could be used to remove remaining IgG and/or IgM (e.g. by protein A affinity chromatography, CaptureSelect IgM), and/or a second ion exchange chromatography could be used for separation of impurities (e.g. anion exchanger, mostly preferably monolith Ethylen di-amine (EDA)). Other steps can be devised by the skilled person to derive the desired purity.

In addition, steps to remove any pathogens, such as viruses or prion proteins, will be included in any commercial process. Such process steps are well known to the skilled person and may be chosen from methods such as nanofiltration, solvent/detergent treatment, pasteurization, and others.

The invention also provides the use of an anion exchange chromatography for the separation of monomeric IgA, which is eluted in the first elution step, from dimeric IgA, which is eluted in the second elution step. It is envisaged that the same could also apply, with suitable adjustments, in particular to the starting materials, to other immunoglobulin isotypes. It is challenging for a process that can be carried out on an industrial scale, to provide the separation of monomeric and dimeric or polymeric immunoglobulin, because the properties of the proteins that need to be separated are very similar and not usually amenable to separation by processes that are suitable for use on an industrial scale.

A further aspect of the invention is a composition obtainable by a method of the invention, and products obtained therefrom. Such a composition may be further processed, for example by further purification steps, and/or by formulation. For example, pharmaceutically acceptable excipients or carriers may be added, a stabilizer may be added if desired, a viscosity enhancing or a viscosity-reducing agent may be added as desired. Lyophilization is also an option. A suitable formulation will be chosen depending on the desired medical use of the product.

In a preferred embodiment of the invention, the IgA is obtained from side fractions and/or waste material that is obtainable during a process of purifying IgG from human plasma. Typically, plasma samples from multiple donors are pooled, and frozen until use. The plasma is then thawed, centrifuged, and ethanol fractionation is performed according to Cohn, or Kistler Nitschmann, or variations thereof on the supernatant (cryo-poor plasma). Generally, the pH is adjusted to a certain range and ethanol is added to a certain concentration, a precipitate forms during several hours of incubation, typically at 4° C., the precipitate and the soluble part are separated and used for further processing. This step is typically repeated on the soluble part with a higher ethanol concentration, etc., until the desired precipitates and solutions are obtained.

The immunoglobulin-containing precipitates are typically solubilised using a 0.1 to 0.3 M, preferably a 0.2 M acetate buffer (pH 4.8), with agitation, overnight. Octanoic acid precipitation is then carried out, and the supernatant is further processed for the purification of IgG. The precipitate contains IgA and can be solubilised and then further processed according to the methods of the invention.

As mentioned above, the supernatant is used to further purify plasma IgG. Typically, a buffer change is carried out, and the material is then applied to an anion exchange chromatography. The purified IgG is collected in the flow-through, and if it is only desired to purify IgG, the proteins bound to the anion exchanger are removed during the cleaning procedure with harsh conditions (e.g. 1 M NaCl or 1 M NaOH), and are discarded.

However, if it is desired to additionally purify IgA, the anion exchanger can then be eluted as described above to obtain eluates enriched for monomeric and/or dimeric IgA. If desired, IgM can also be recovered. Typically, after suitable washing steps, a pre-elution is carried out, using phosphate/acetate buffer, pH 6.0. The material collected during the pre-elution is called F3, and contains mainly IgG.

Typically, a first elution is then carried out, using a tartrate/acetate buffer, pH 7.3 to 7.8. During this step, material F4 is eluted, which is enriched in monomeric IgA, but also contains IgG. Advantageously, no IgM is found in this material. As disclosed above, other buffers can also be used within the invention.

If desired, a second elution step is then carried out, using a citrate/phosphate buffer at a pH of about 5. Other buffers that can be used according to the invention for this step are disclosed above. The second elution provides material F5, which contains IgG, IgA and IgM. In this material dimeric IgA is enriched.

Pathogen inactivation and/or removal steps, such as nanofiltration, will be incorporated in these processes at appropriate stages to ensure the safety of the resulting material. Many methods for pathogen inactivation and removal have been described, and the skilled person will be able to incorporate such steps into the process without undue burden.

As mentioned above, the octanoic acid precipitate is also a suitable starting material for the method of the invention. The inventors have advantageously found that solubilisation with a solution of low conductivity at a pH between 3.5 and 6 or 7 to 9.5, preferentially brings IgA and IgG into solution. For example, the buffer may be acetate or phosphate buffer, although other buffers can be used.

A preferred embodiment of the invention is a method for the separation of IgA (and IgM) from an IgA-comprising composition and/or immunoglobulin-containing material, whereby the method is characterized in that:
(i) an IgA-comprising composition is loaded to macroporous anion-exchange resin,
(ii) IgA is isolated from the exchange resin, after sequential selective desorption/elution,
(iii) the sequential elution consists of
A) a pre-elution step at a weakly acidic to natural pH, resulting in an IgG fraction
B) a first elution step using a dicarboxylic acid or a dihydroxy-dicarboxylic acid or salts thereof and /or phosphate at slightly alkaline pH, resulting in a fraction containing at least 40 to 60% of monomeric IgA and up to 60% of IgG. This fraction is IgM depleted.
C) a second elution step using either hydroxy-tricarboxylic acid or salts thereof, benzenesulfonic acid, or benzoic acid and salts of hydrogen sulfates or mixtures thereof at acidic pH, resulting in a fraction containing approximately 45% IgM; 25% IgA (predominantly di-/polymeric), 25% IgG and 5% contaminants other than immunoglobulins.

The method can be optionally integrated into various processes of plasma fractionation in a very straightforward manner, and always leads to the same intermediate IgA compositions.

From the resulting fractions, highly purified IgA (and IgM) concentrates can be produced for possible therapeutic applications. The sequential and selective elution has already been evaluated at pilot plant scale.

DEFINITIONS

The term "IgA-comprising composition" relates to any liquid composition that contains IgA. In particular, these compositions will be biological fluids such as saliva, tears, or mucus, any plasma fraction or side/waste fraction that may be obtained, e.g. during the processing of plasma to purify plasma proteins such as IgG for therapeutic purposes. The term also includes compositions of IgA produced in vitro, e.g. monoclonal IgA or recombinantly produced IgA, e.g. IgA secreted by cell lines.

The term "enrich" or "enrichment" in the context of the present invention relates to a significant increase of the amount of a target protein relative to the total protein content in a composition, e.g. after a purification step. An enrichment would be achieved if the purity of the target protein increased by at least 20%, preferably by at least 30%, even more preferably by at least 50%, most preferably by more than 75%.

The term "pure" relates to a composition essentially comprising only the target protein. In the context of the present invention, a solution would be a pure IgA solution if it contains more than 90% (w/w) IgA, preferably more than 95% IgA, more preferably more than 98% IgA.

The term "ion exchange chromatography" relates to a process that allows the separation of ions based on their charge. In the present invention, anion exchange chromatography is used, whereby negatively charged molecules (e.g. proteins in a solution at a pH, where they exhibit negatively charged domains) are selectively retained by cationic groups (anion exchange ligands), which are covalently bound to a solid matrix. The solid matrix can be any suitable carrier material, and can be in the shape of beads, membranes or other suitable solid support configuration. Typically, the solid matrix would be in the form of beads, and would be used as a column. However, other ways of performing anion exchange are also included in the present invention. A strong anion exchanger is charged over a broad pH range, whereas the charge of a weak anion exchanger would vary with pH.

To "load onto an anion exchanger" means bringing the solution that is to be subjected to anion exchange chromatography in contact with the anion exchange ligands on their solid support. Typically in the present context, the term would refer to the column feed during the chromatography step. However, as already mentioned above, the invention is not limited to a column configuration for the anion exchanger. For example, it could also be carried out in batch mode.

The term "flow-through" refers to the material that is not retained during the chromatography step. In the context of the present invention, it is the fraction that is unbound or only loosely bound by the anion exchanger. The flow-through for any given anion exchanger will vary according to the buffer system used.

The term "eluate" refers to the material that was bound by the anion exchanger, but is then released from the anion exchanger after a change of conditions, i.e. after an "elution solution" is applied to the anion exchanger. It is typically collected in fractions after the elution solution is applied to the anion exchanger.

The term "neutral pH" relates to a pH of about 7. Typically a range of 6.0 to 7.5 would be considered as neutral, preferably a range of 6.5 to 7.5, more preferably a range of 6.8 to 7.2, most preferably a range of 6.9 to 7.1.

The term "weakly acidic" would refer to a pH range of about 4.0 to 6.5, preferably a range of 5.0 to 6.0, more preferably a range of 5.5 to 6.0.

The term "low conductivity" refers to a conductivity of below 15 mS/cm, preferably below 10 mS/cm.

The term "essentially devoid of IgM" refers to less than 10% IgM (w/w), preferably less than 5%, even more preferably less than 2%, most preferably less than 1% IgM of the total protein present.

The term "biological fluid" includes liquids originating from inside the bodies of vertebrates, including fluids that are excreted or secreted from the body, such as milk, saliva, mucus, tears.

The term "plasma" refers to the liquid component of blood (about 55% of the total blood volume). It contains plasma proteins such as albumin, immunoglobulins (antibodies), clotting factors, hormones, and other components such as glucose or mineral ions.

The term "serum" relates to plasma depleted of fibrinogen and clotting factors, i.e. the liquid fraction after clotting occurs.

The term "plasma fractionation" relates to separation processes of plasma proteins. Typically it relates to the initial processing steps in the industrial scale purification processes of plasma proteins that allow a first separation of the main classes of plasma proteins which are then subjected to further processes for purification. Typically the fractionation is carried out by ethanol as described by Cohn, Oncley or Kistler Nitschmann or variants thereof. Other fractionation methods are based on precipitation with other agents such as octanoic acid, polyethylene glycol, or ammonium sulfate.

The term "intermediate precipitate" relates to a precipitate that is a result of the plasma fractionation or other precipitations that may be carried out during the downstream purification processes for plasma proteins. It typically contains a mixture of different plasma proteins.

The term "solubilisation of a precipitate" relates to the addition of liquid, typically a buffer, to a precipitate to bring the proteins contained in the precipitate back in solution for further purification steps.

The term "side/waste fraction" relates to an intermediate of plasma fractionation or down-stream processes that are normally not further processed, i.e. are discarded.

The invention will now be illustrated by the following non-limiting examples, with reference to the following figures:

FIG. 1: Flow diagram of the IgA enrichment process based on different intermediate precipitate of plasma fractionation or a side fraction obtained during purification of IgG from plasma. Two starting materials have been exemplified (Method 1 in example 1 and Method 2 in example 2).

Figure 2:
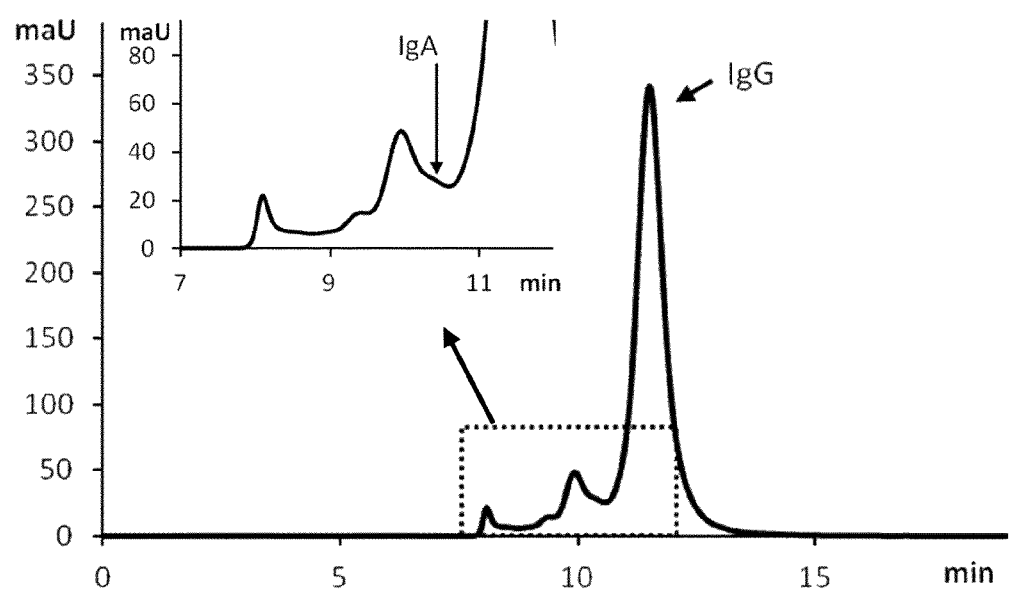

FIG. 2: HPLC analysis of the composition of the loaded material (feed stock) for the anion exchange chromatography, according to Method 1 shown in FIG. 1. The x-axis shows the elution time, the y-axis shows the absorbance at 280 nm (mAu milli-absorption unit).

Figure 3:
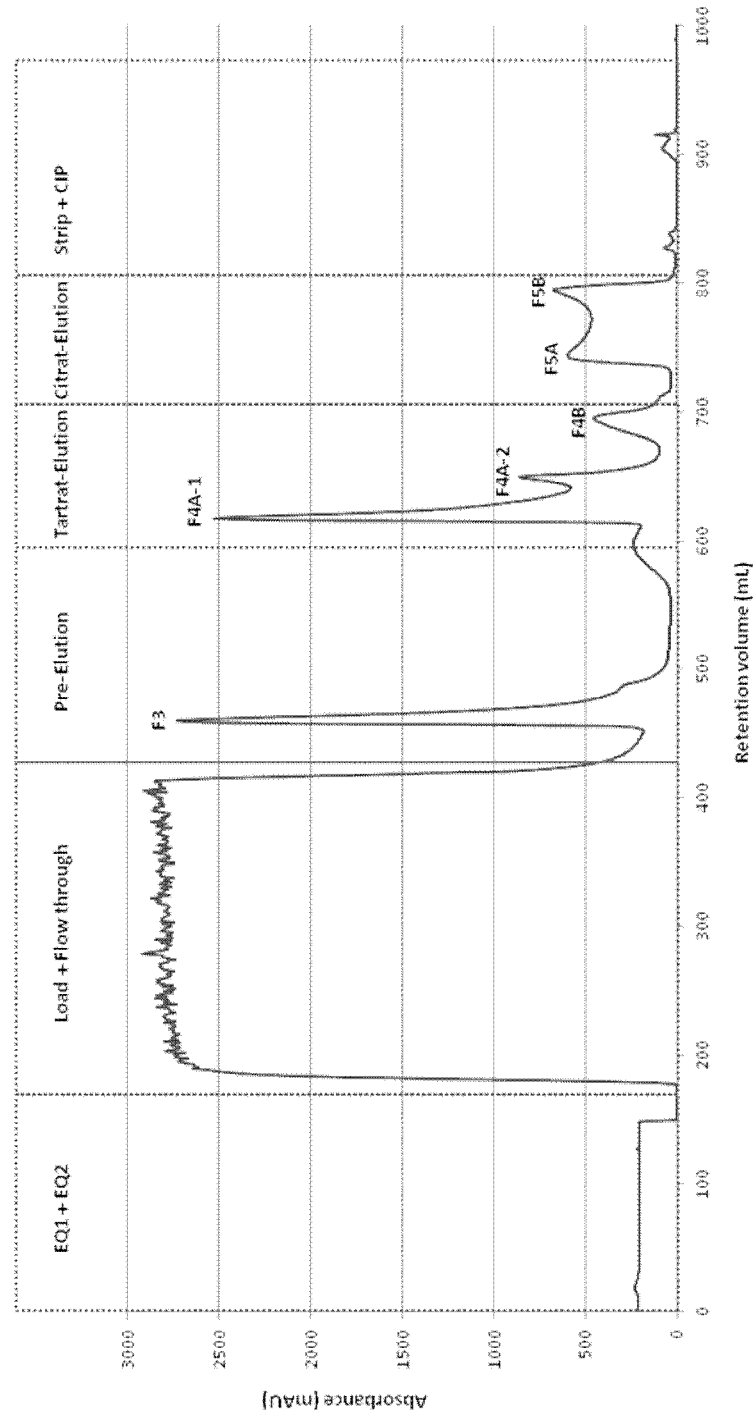

FIG. 3: Elution profile of the anion exchange column, showing the retention volume in milliliter on the x-axis, and the absorbance at 280 nm (mAu: milli-absorption unit) on the y-axis. The elution solutions are indicated above the profile, the vertical lines indicate the change of solution applied to the column.

Figure 4:
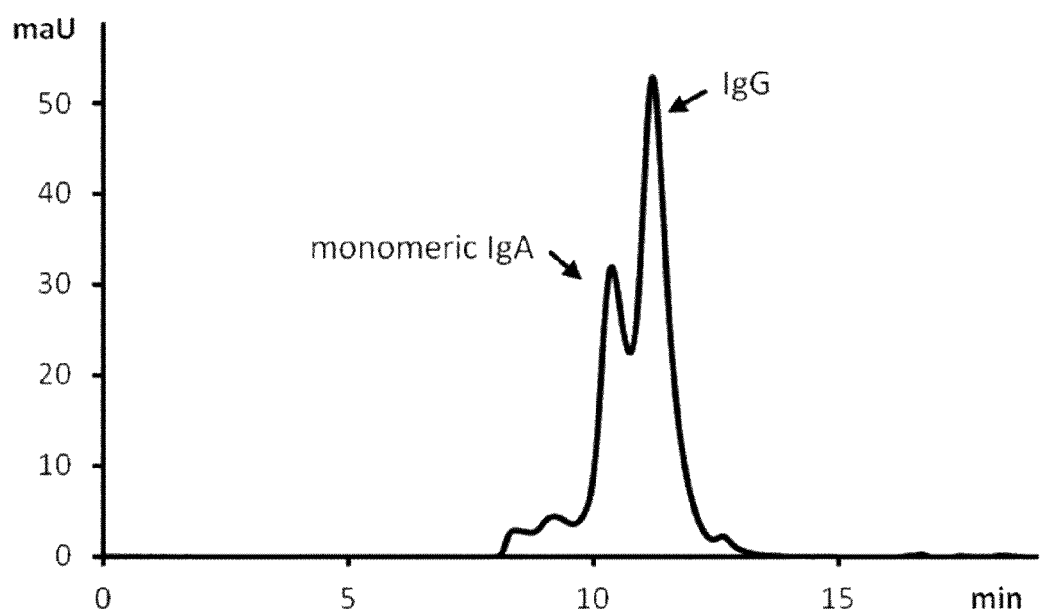

FIG. 4: HPLC analysis of the composition of fraction F4A, according to Method 1.

Figure 5:
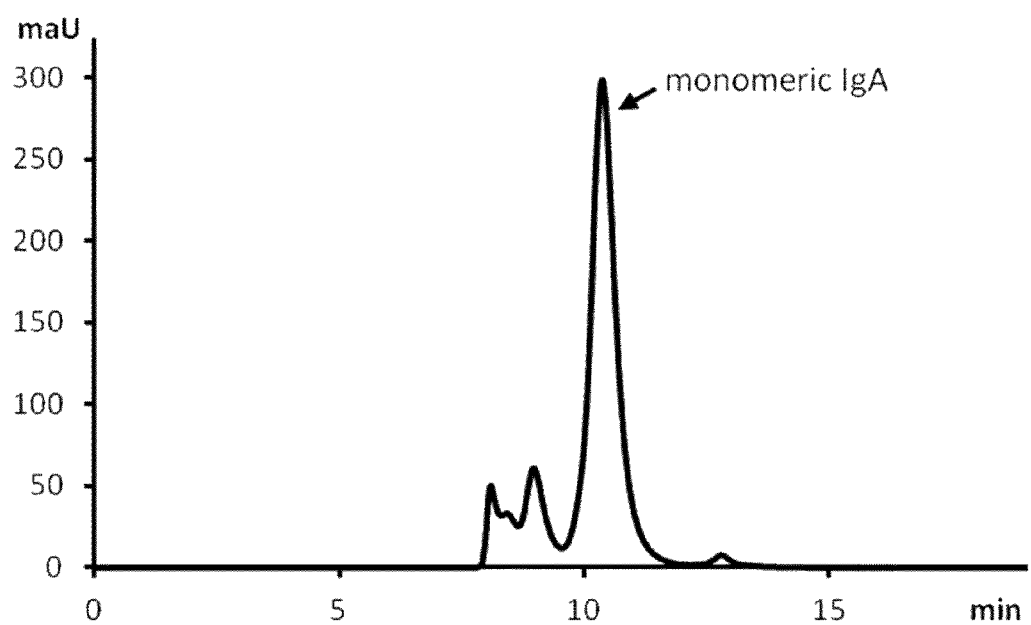

FIG. 5: HPLC analysis of the composition of F4 after removal of IgG by affinity chromatography.

Figure 6:
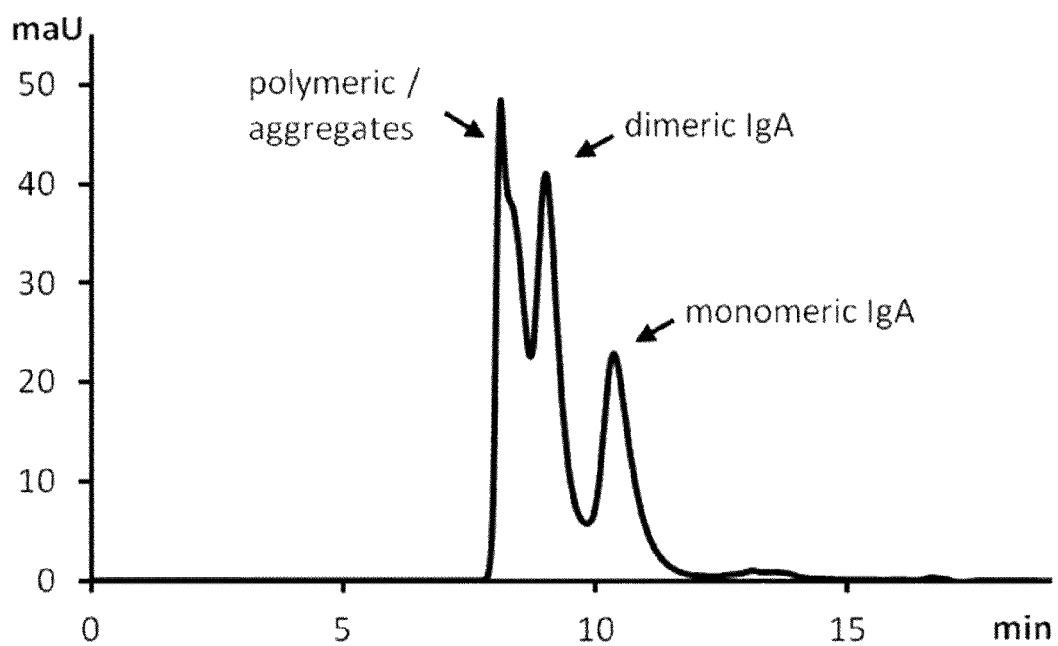
Figure 7C:
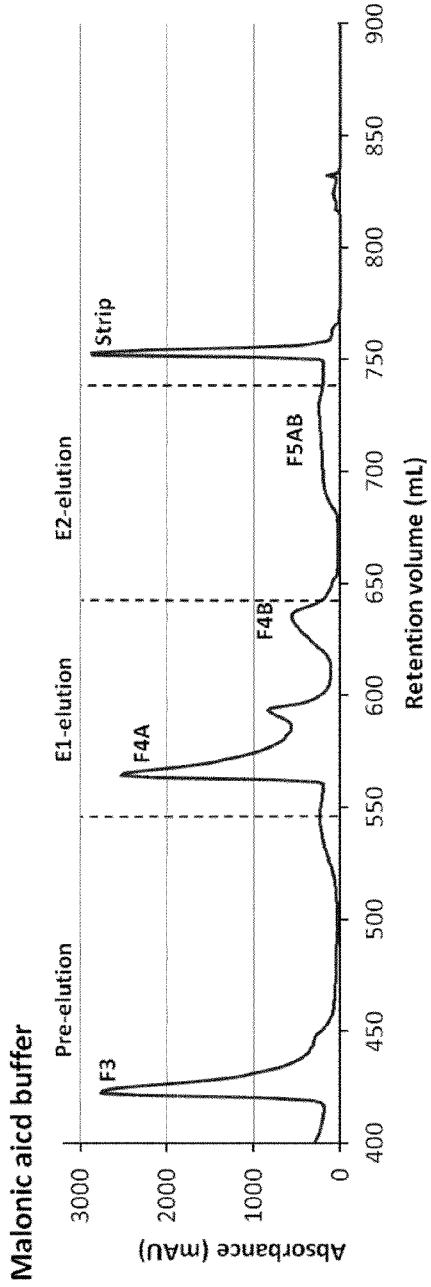
Figure 7D:
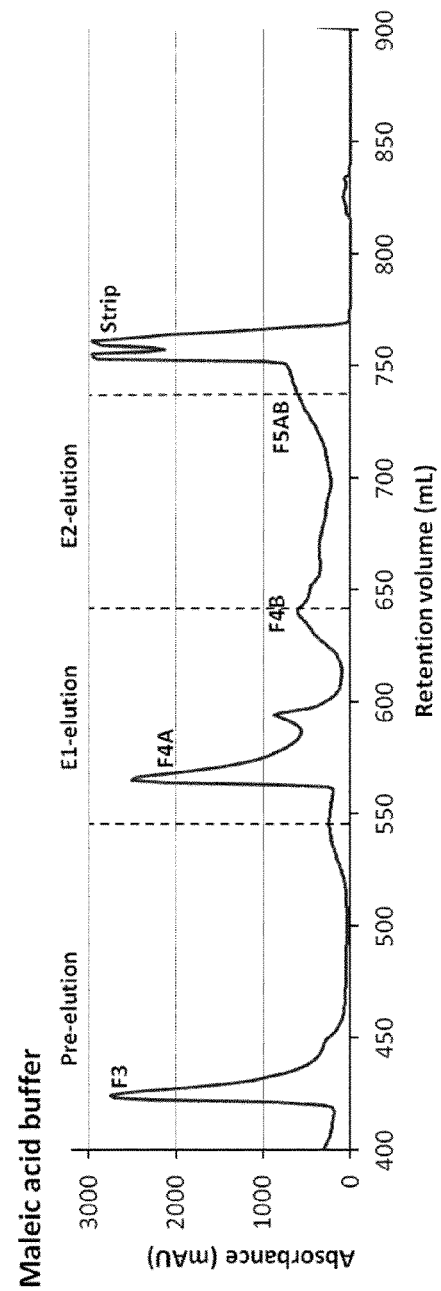
Figure 7E:
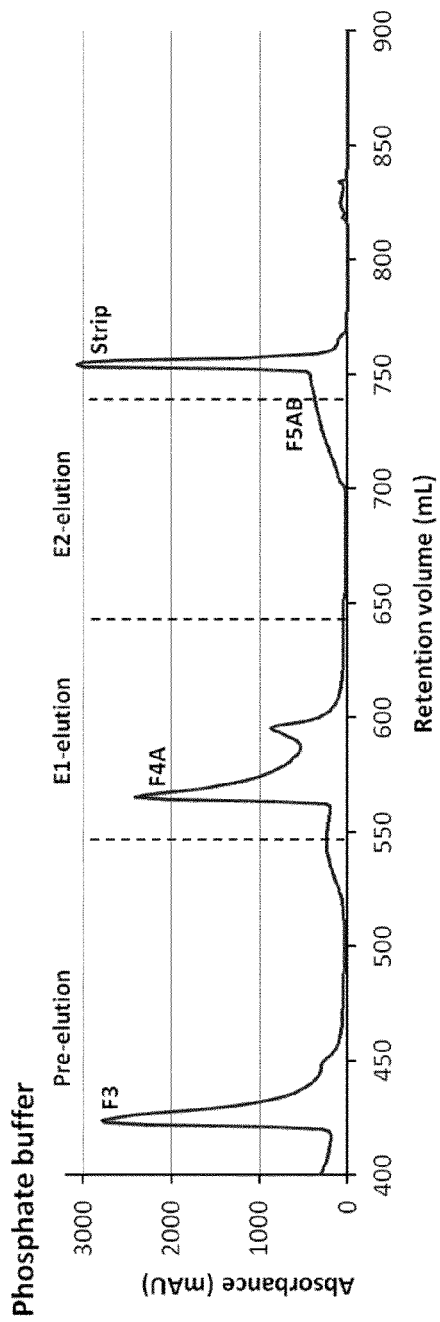
Figure 7F:
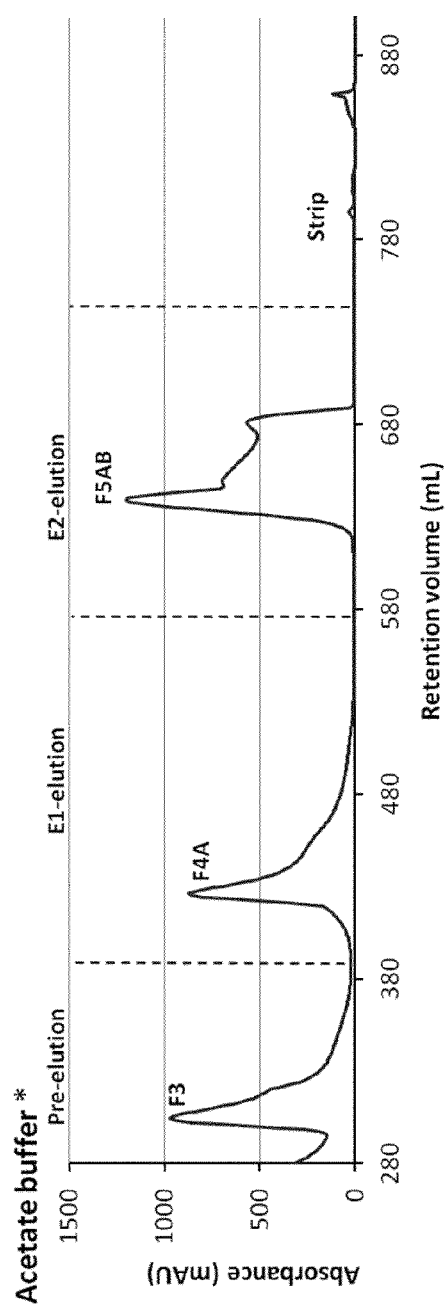
Figure 8A:
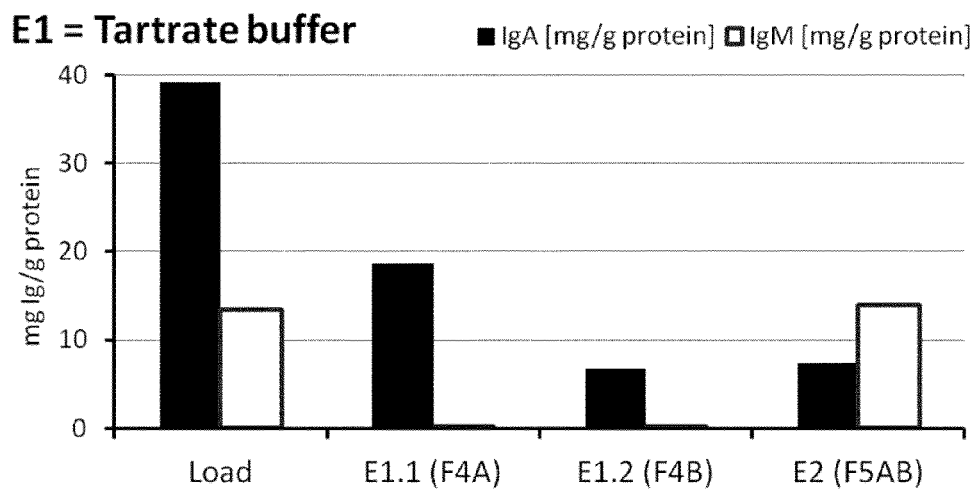
Figure 8B:
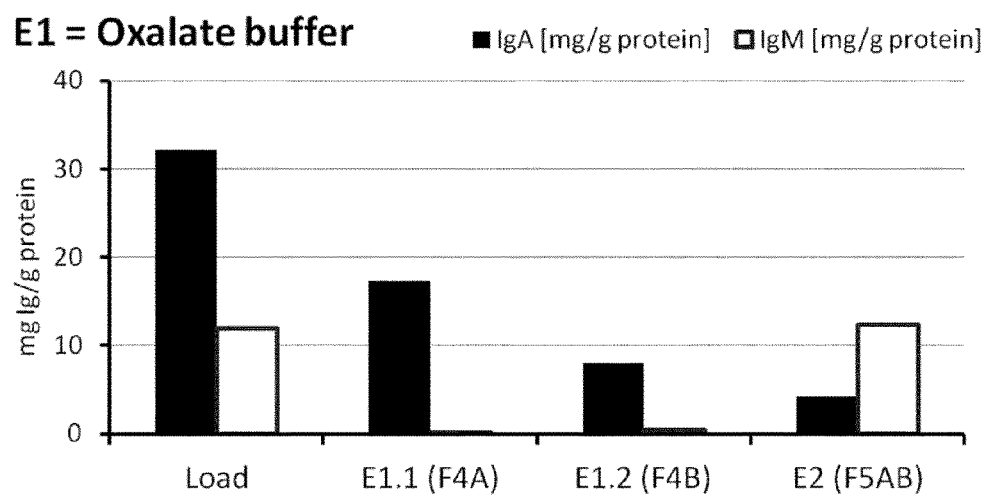
Figure 8C:
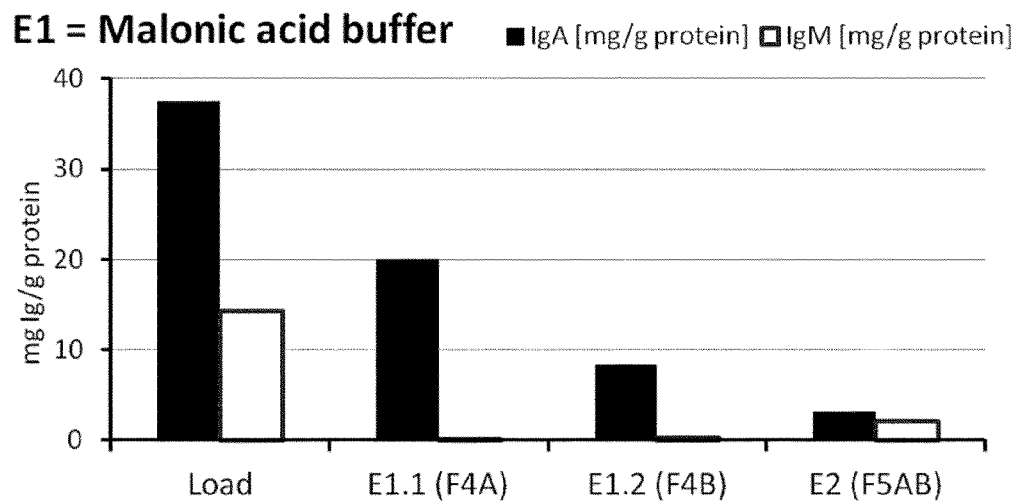
Figure 8D:
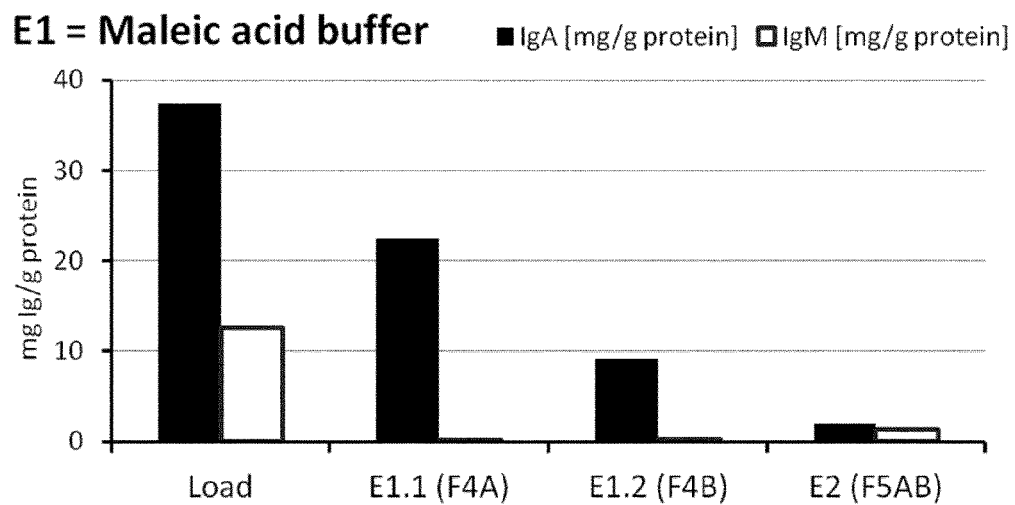
Figure 8E:
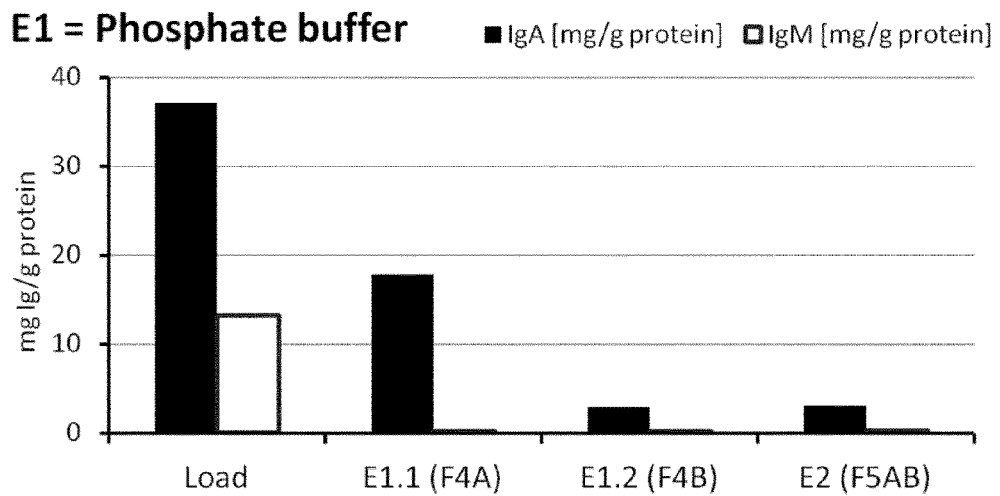
Figure 8F:
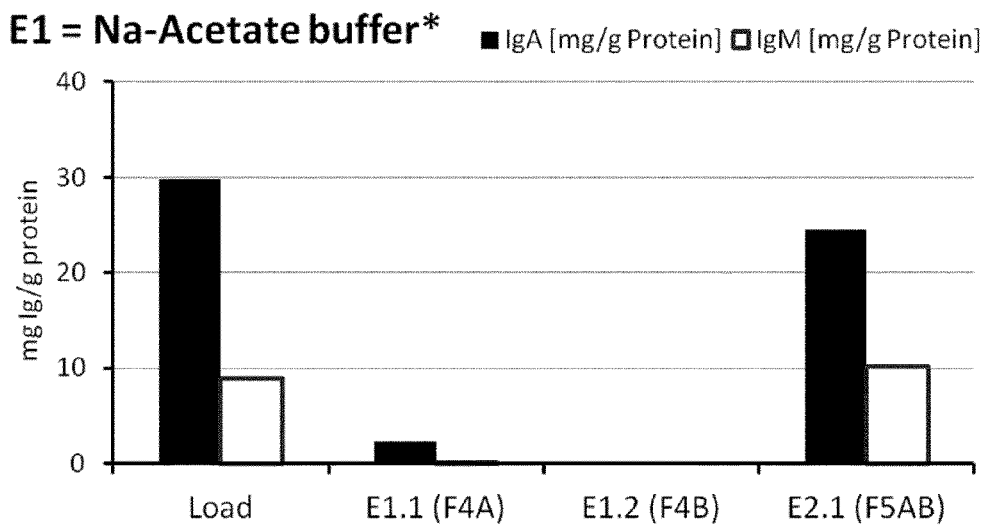

FIG. 6: HPLC analysis of the composition of fraction F5 of IgG and IgM by affinity chromatography.

FIG. 7: Elution profiles of the process of anion exchange column, using different buffers as elution buffer 1. The dashed vertical lines indicate the change of solution applied to the column. *The load for the acetate buffer elution was reduced.

FIG. 8: Analysis of the content of IgA and IgM in the fractions obtained when carrying out elution 1 with different elution buffers relative to the total loaded protein.

EXAMPLES

The following examples serve to illustrate the invention, but are not intended to limit the invention.

In the following examples, materials that originate from the IgG purification process from plasma and/or plasma fractions are used as the starting material for the present invention. FIG. 1 shows a flow chart of the IgG purification process, and indicates examples of where in the process an IgA purification method according to the invention can be introduced.

Briefly, the following steps are carried out to purify IgG from plasma: Plasma or cryo-poor plasma are subjected to cold ethanol fractionation, e.g. according to Cohn or Kistler-Nitschmann, and the immunoglobulin-containing fractions are further processed. An octanoic acid precipitation is carried out and the suspension containing most of the IgG is then subjected to filtration, virus inactivation, and anion exchange (AIEX) chromatography. Most of the IgG is collected in the AIEX flowthrough and further processed, including final formulation and packaging.

As shown in FIG. 1, an IgA purification method according to the invention can be branched off from the cold ethanol fractionations, e.g. FI+II+III, the supernatant of FI, FII+III, precipitate A, or subfractions thereof. However, preferably, material solubilised from the octanoic acid precipitate (octanoic acid cake) is subjected to the methods of the invention, or the material bound to the anion exchange column is subjected to sequential elution according to the present invention to obtain plasma IgA. The latter materials are preferred as they are currently discarded. Carrying out the process for IgA purification from these materials does not interfere with the IgG process, so that the yield of IgG or other plasma proteins is not decreased or compromised in any way. Nevertheless, the invention is not limited to those starting materials.

Example 1

Sequential Elution of IgA from an Anion Exchange (AIEX) Column Using Tartrate Buffer as Elution Buffer 1

The process for the purification of IgG from plasma was carried out essentially as shown in FIG. 1 and briefly described above. In the IgG purification process the AIEX column (MPHQ) is equilibrated with two buffers, using 0.78 M sodium acetate, pH 4.0±0.1, conductivity 8-10 mS/cm for the first 2 column volume (CV), followed by 8 CV 10 mM sodium acetate, pH 6.5±0.1, conductivity 0.8-1.2 mS/cm. FIG. 2 shows the AIEX feedstock composition, which is loaded on the AIEX column (about 180 g protein per L resin) and afterwards washed with 2 CV equilibration buffer 2. After this step the AIEX column was subjected to sequential elution.

Therefore, a pre-elution step was carried out using 8 CV phosphate acetate buffer (10 mM phosphate+30 mM sodium acetate, pH 6.0, conductivity 2-7 mS/cm). As can be seen in FIG. 3, during the pre-elution step, fraction F3 is eluted, which contains mainly IgG.

After this pre-elution step the buffer was changed to the first elution buffer (5-8 CV 55 mM tartrate, 5 mM sodium acetate, pH 7.6±0.2, conductivity 5-15 mS/cm). After switching to the tartrate buffer fraction F4 is collected, which contains IgG and IgA in a ratio of about 60:40, and is essentially devoid of IgM. IgA eluted in this fraction is mainly monomeric IgA. As can be seen in FIG. 3, several subfractions (peak fractions) can be collected in this step if desired. FIG. 4 shows the composition of the F4 subfraction F4A. However, all subfractions contain only IgG and monomeric IgA in various ratios.

Thereafter, 6 CV 50 mM phosphate and 25 mM citrate (pH 5.0, conductivity 5-15 mS/cm) as second elution buffer was applied. After switching to the second elution buffer fraction F5 is eluted, which can be collected in two subfractions (peak fractions) (FIG. 3), enriched in dimeric IgA. Fraction F5 contains IgM, IgA and IgG in the ratio 20-30% IgA (predominantly di-/polymeric), 35-50% IgM and 20-35% IgG.

Fractions F4 and F5 were polished by affinity chromatography (one or two steps) to selectively remove IgG and IgM. HPLC analysis showed that the obtained product from fraction F4 is highly pure monomeric IgA (FIG. 5), whereas fraction F5 is enriched in dimeric IgA (FIG. 6). Therefore, this elution method provides an excellent enrichment for monomeric IgA in fraction F4 and dimeric IgA in fraction F5.

Other AIEX materials (Fractogel, HyperCel Star AX, Q HyperCel) were also tested and have given similar elution profiles.

Example 2

Testing Different Buffers for the First Elution Step

Several different buffers were evaluated in the first elution step and compared to the tartrate buffer elution profile.

The experiment was carried out essentially as described in Example 1, with a protein load between 100 to 180 g protein per L AIEX resin. However, for the first elution, tartrate buffer was replaced by oxalate, malonate, maleate, phosphate, acetate buffer (55 mM of each substance+5 mM sodium acetate, pH 7.6±0.2).

The resulting elution profiles are shown in FIG. 7. Fraction F4 appears to be similar for all buffers as long as substances with at least 2 acid groups were used in the first elution, whereas the acetate and phosphate elution profiles look quite different. However, the first elution also affects the second elution with citrate buffer. It can be seen that oxalate buffer yields a similar F5 peak (FIG. 7). With malonate, maleate or phosphate buffers, the IgM is not eluted during the second elution. With acetate buffer as the first elution buffer, almost all IgA and the total amount of IgM is eluted in F5.

The amount of IgA and IgM in these fractions relative to the total loaded protein is illustrated in FIG. 8. Tartrate and oxalate provide the preferred elution profile, where the monomeric IgA is eluted in F4, and IgM and dimeric IgA are eluted in F5. Only the elution with the hydroxydicarbon acids resulted in all 3 F4 subfractions and monomeric IgA elution. The first elution step using phosphate buffer showed only 2 subfractions and an extenuated IgA elution, whereas acetate buffer generated an F4 peak with a small amount of IgA. If the first elution is done with malonate, maleate or phosphate buffer a large peak is obtained in the strip fractions, where harsh elution conditions are used (1 M NaCl)

The immunoglobulin content in the different fractions are also shown in Table 1:

|  | IgG* [mg] | IgA** [mg] | IgM** [mg] |
| --- | --- | --- | --- |
| E1: Tartrate buffer |  |  |  |
| Load | 3250.8 | 139.51 | 47.76 |
| pre E (F3) | 137.2 | 3.79 | 0.04 |
| E1 (F4) | 117.6 | 90.27 | 0.87 |
| E2 (F5) | 37.32 | 26.29 | 49.42 |
| STRIP | 0 | 0.00 | 0.00 |
| E1: Oxalate buffer |  |  |  |
| Load | 3322.7 | 114.78 | 42.60 |
| pre E (F3) | 150.2 | 10.55 | 0.09 |
| E1 (F4) | 128.8 | 90.38 | 1.72 |
| E2 (F5) | 35.77 | 14.94 | 44.14 |
| STRIP | 0 | 1.90 | 2.79 |
| E1: Malonic acid buffer |  |  |  |
| Load | 3325.8 | 133.68 | 50.99 |
| pre E (F3) | 140.2 | 5.94 | 0.14 |
| E1 (F4) | 123.4 | 101.25 | 1.38 |
| E2 (F5) | 20.26 | 11.24 | 7.22 |
| STRIP | 16.13 | 16.30 | 45.70 |
| E1: Maleic acid buffer |  |  |  |
| Load | 3331.5 | 132.98 | 44.98 |
| pre E (F3) | 141.2 | 4.95 | 0.06 |
| E1 (F4) | 119.7 | 112.80 | 1.23 |
| E2 (F5) | 11.43 | 7.17 | 4.75 |
| STRIP | 26.16 | 24.54 | 48.32 |
| E1: Phosphate buffer |  |  |  |
| Load | 3412.2 | 132.19 | 46.98 |
| pre E (F3) | 145.15 | 5.69 | 0.05 |
| E1 (F4) | 109.1 | 73.61 | 0.34 |
| E2 (F5B) | 18.1 | 10.78 | 0.92 |
| STRIP | 34.4 | 42.09 | 45.80 |
| E1: Acetate buffer* |  |  |  |
| Load | 1210 | 39.92 | 11.90 |
| pre E (F3) | 55.34 | 0.75 | — |
| E1 (F4) | 54.68 | 3.03 | 0.02 |
| E2 (F5) | 58.55 | 32.81 | 13.64 |
| STRIP | — | — | — |

*Nephelometric analysis method,
**ELISA analysis method

Advantageously we found that the pH of such buffers, for example the tartrate buffer, can be stabilized by addition of Tris buffer pH 7.6±0.4, to a final concentration of 1 to 20 mM, preferably 2 to 15 mM, more preferably 5 to 10 mM.

Example 3

Solubilisation of IgA from the Octanoic Acid Precipitate

As shown in FIG. 1, the octanoic acid precipitate (OA cake) is another waste fraction incurring during the IgG purification process. This precipitate was found to contain significant amounts of IgA and is therefore a good starting material for the purification of IgA.

The OA cake was mixed with 0.15M phosphate buffer, pH 4.8 at a ratio of 1:6 (OA precipitate to buffer). However, other buffers can also be used for IgA extraction, e.g. Tris buffer. The solubilised material was subjected to filtration, and then loaded on an AIEX column (MPHQ). The column was then sequentially eluted essentially as described in Example 1. The elution profile looks essentially as already shown in FIG. 3.

The composition of the IgA-comprising feedstock for the AIEX column varies in the ratio of IgG to IgA in comparison to the described example 1. As shown in Table 2, the ratio of IgG to IgA in fraction F4 has shifted in favor of IgA (15%:85%). Also the amount of IgA in the pre-elution fraction F3 is increased. Both fractions are devoid of IgM.

The elution of dimeric/polymeric compounds is limited due to the composition of the start material.

The immunoglobulin content in the different fractions is also shown in Table 2:

|  | IgG* [mg] | IgA** [mg] | IgM** [mg] |
| --- | --- | --- | --- |
| Load | 380.80 | 271.86 | 4.84 |
| pre E (F3) | 28.17 | 57.34 | 0.01 |
| E1 (F4) | 20.09 | 109.78 | 0.07 |
| E2 (F5) | 7.43 | 12.80 | 6.32 |
| STRIP | 0.30 | 1.08 | 0.03 |

*Nephelometric analysis method,
**ELISA analysis method

To show that this works with other IgA-comprising precipitates as well, we also tested other precipitates. IgA could also be solubilised from two different ethanol precipitates and subjected to AIEX chromatography, and very similar elution profiles were obtained with the method of the invention.

Example 4

Polishing of Monomeric IgA

The sequential elution resulted in an enriched monomeric IgA fraction (F4) containing IgG as contaminant. A polishing step was carried out by a selective removal of IgG by affinity chromatography (IgSelect).

The fraction F4 was collected in two subfractions F4A and F4B (FIG. 3). However, the obtained F4A fraction was subjected to ultrafiltration/diafiltration to concentrate the protein and transfer it to a common buffer system with neutral pH, preferably PBS (phosphate buffered saline). This protein solution was used as feedstock for the affinity chromatography. IgA does not bind to the affinity resin and was collected in the flow through fraction. Bound IgG was eluted with 0.1 M glycine buffer, pH 3.0. Finally the IgA product can be formulated into a stable, pharmaceutical composition. FIG. 5 shows the polished IgA fraction without IgG (and IgM).

The invention claimed is:
1. A method for enriching IgA from an IgA-comprising composition, comprising the following steps:
   (a) loading the composition onto an anion exchanger under conditions that allow the IgA to bind;
   (b) applying an alkaline elution solution comprising a substance with at least 2 acid groups;

(c) optionally applying an acidic elution solution that comprises a strong competitor for the anion exchanger, wherein protein eluted during step (b) is enriched for monomeric IgA by at least 50% and the substance with at least 2 acid groups is not phosphate.

2. The method of claim 1, wherein between steps (a) and (b), a pre-elution step (a1) is carried out by applying a low conductivity solution to the anion exchanger.

3. The method of claim 2, wherein step (a1) is performed at a weakly acidic to neutral pH.

4. The method of claim 1, wherein the substance in step (b) comprises a multivalent hydroxy-carboxylic acid with at least 2 carboxyl groups or salts thereof.

5. The method of claim 1, wherein the substance in step (b) comprises a dihydroxy-dicarboxylic acid and/or dicarboxylic acid or salt thereof, or a hydroxy-tricarboxylic acid or salt thereof.

6. The method of claim 1, wherein the substance in step (b) comprises tartaric acid/tartrate, oxalic acid/oxalate, malonic acid/malonate, or maleic acid/maleate.

7. The method of claim 1, wherein the substance in step (b) comprises tartaric acid/tartrate or oxalic acid/oxalate.

8. The method of claim 7, wherein the protein eluted in step (c) is enriched in dimeric IgA.

9. The method of claim 1, wherein the eluate collected during step (b) is essentially devoid of IgM.

10. The method of claim 1, wherein the strong competitor for the anion exchanger in step (c) comprises citrate, benzenesulfonic acid, benzoic acid or salts of hydrogen sulfates or mixtures thereof.

11. The method of claim 10, wherein the strong competitor for the anion exchanger is citrate.

12. The method of claim 1, wherein the anion exchanger is a strong anion exchanger or a weak anion exchanger.

13. The method of claim 12, wherein the anion exchanger comprises an anion exchange ligand.

14. The method of claim 13, wherein the anion exchange ligand comprises quaternary ammonium, quaternary aminoethyl, diethylaminoethyl, trimethylaminoethyl, or dimethylaminoethyl.

15. The method of claim 1, wherein the IgA-comprising composition is or is derived from blood, serum, plasma or other biological fluids.

16. The method of claim 15, wherein the IgA-comprising composition is a solution of an intermediate precipitate of plasma fractionation or a side fraction obtained during purification of IgG from plasma.

17. The method of claim 15, wherein the IgA-comprising composition is an intermediate in an IgG purification process, and wherein step (a) and (b) of the method of claim 1 are performed on an anion exchanger that is part of the IgG production process.

18. The method of claim 15, wherein the IgA-comprising composition is obtained by solubilising a precipitate.

19. The method of claim 18, wherein the precipitate is an octanoic acid precipitate obtained during IgG purification.

20. The method of claim 18, wherein the solubilisation step selectively brings IgA and IgG into solution.

21. The method of claim 19, wherein the solubilisation is carried out using a solution with a conductivity of between 1 and 15 mS/cm, and a pH of 3.5 to 6 or 7 to 9.5.

22. The method of claim 21, wherein the solubilisation is carried out with a phosphate buffer, an acetate buffer, a Tris buffer, and/or a combination of two or more of these buffers.

23. The method of claim 22, wherein the buffer is selected from 0.22 M acetate buffer or 0.15 M phosphate buffer, pH 4.8.

24. A method for enriching IgA from an IgA-comprising composition, comprising the following steps:
  (a) loading the IgA-comprising composition in a buffer with pH of 3 to 8 and conductivity of 5 to 50 mS/cm onto an anion exchange resin under conditions that allow the IgA to bind;
  (b) eluting IgA enriched by at least 75% by applying an alkaline elution solution at pH 7.4 to 7.8 comprising a dihydroxy-dicarboxylic acid and/or dicarboxylic acid or salt thereof and/or a hydroxy-tricarboxylic acid or salt thereof at a concentration of 20 to 80 mM.

25. The method of claim 24, wherein the IgA-comprising composition is a solution of an intermediate precipitate of plasma fractionation or a side fraction obtained during purification of IgG from plasma.

26. The method of claim 24, wherein the dihydroxy-dicarboxylic acid or salt thereof is tartaric acid/tartrate or the dicarboxylic acid is oxalic acid/oxalate.

* * * * *